(12) United States Patent
Kaemmerer et al.

(10) Patent No.: US 8,557,975 B2
(45) Date of Patent: Oct. 15, 2013

(54) METHODS AND SEQUENCES TO SUPPRESS PRIMATE HUNTINGTON GENE EXPRESSION

(75) Inventors: William F. Kaemmerer, Medina, MN (US); Michael D. Kaytor, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/601,198

(22) Filed: Aug. 31, 2012

(65) Prior Publication Data

US 2013/0005794 A1    Jan. 3, 2013

Related U.S. Application Data

(63) Continuation of application No. 12/556,888, filed on Sep. 10, 2009, now Pat. No. 8,258,112, which is a continuation of application No. 11/429,491, filed on May 4, 2006, now abandoned.

(60) Provisional application No. 60/678,729, filed on May 6, 2005.

(51) Int. Cl.
*C07H 21/04* (2006.01)
*A61K 48/00* (2006.01)

(52) U.S. Cl.
USPC .................................. 536/24.5; 514/44 R

(58) Field of Classification Search
USPC .................................. 536/24.5; 514/44 R
See application file for complete search history.

(56) References Cited

U.S. PATENT DOCUMENTS 7,829,694 B2 * 11/2010 Kaemmerer ............. 536/24.5
2004/0220132 A1 * 11/2004 Kaemmerer ............. 514/44

* cited by examiner

*Primary Examiner* — Jon E Angell

(57) ABSTRACT

Disclosed herein are sequences, molecules and methods used to suppress the expression of HD genes encoding for huntingtin protein in primates including *Macaca mulatto* and *Homo sapiens*. These sequences, molecules and methods aid in the study of the pathogenesis of HD and can also provide a treatment for this disease.

22 Claims, 24 Drawing Sheets

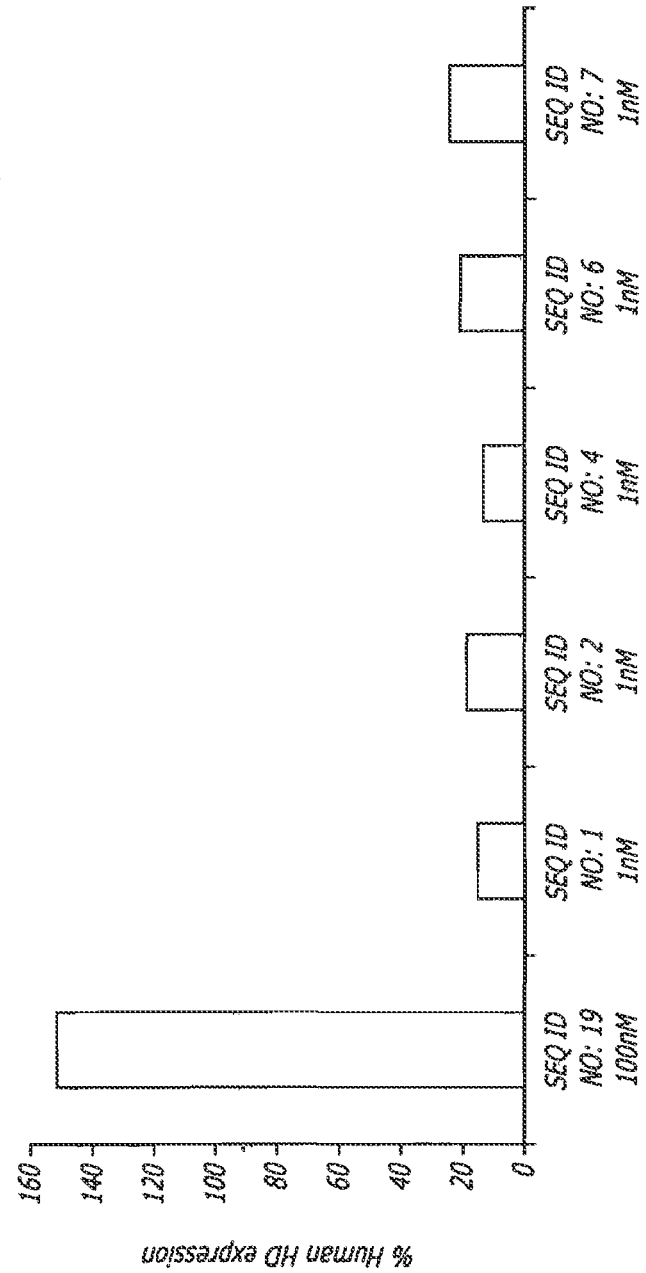

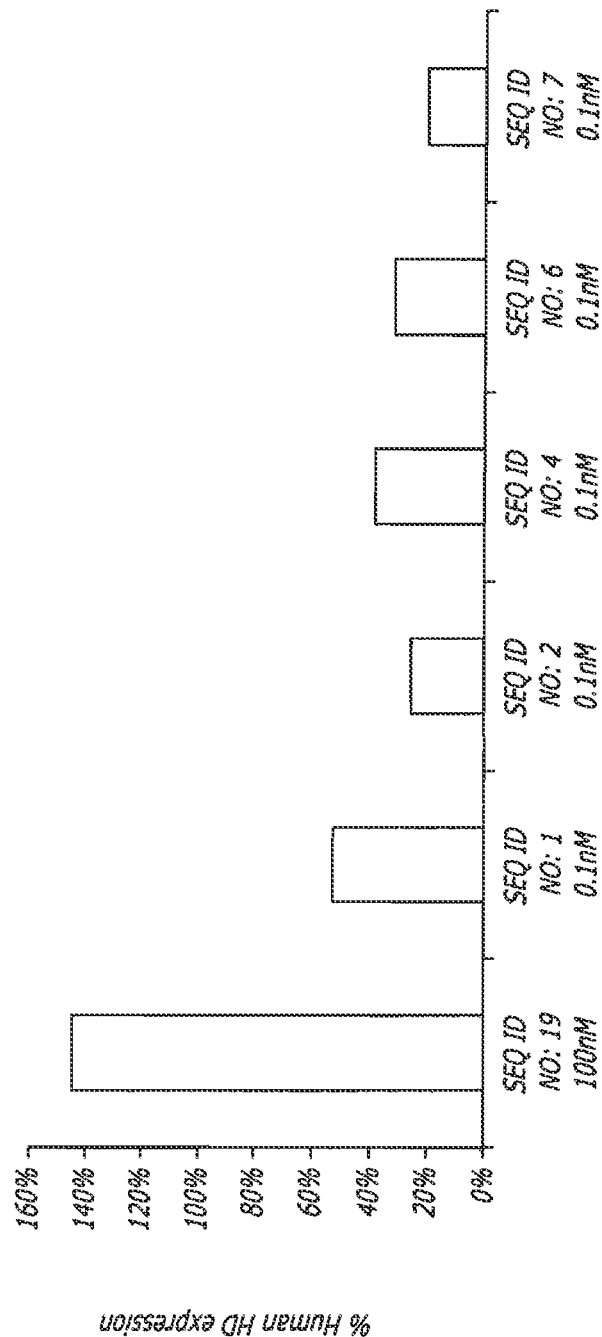

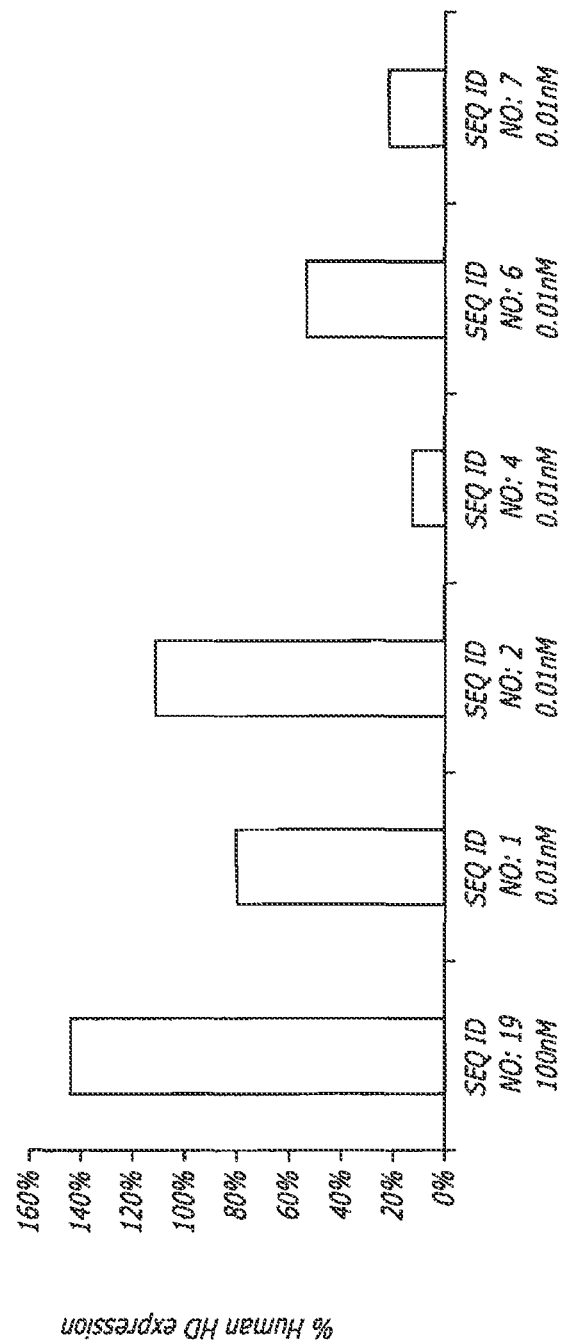

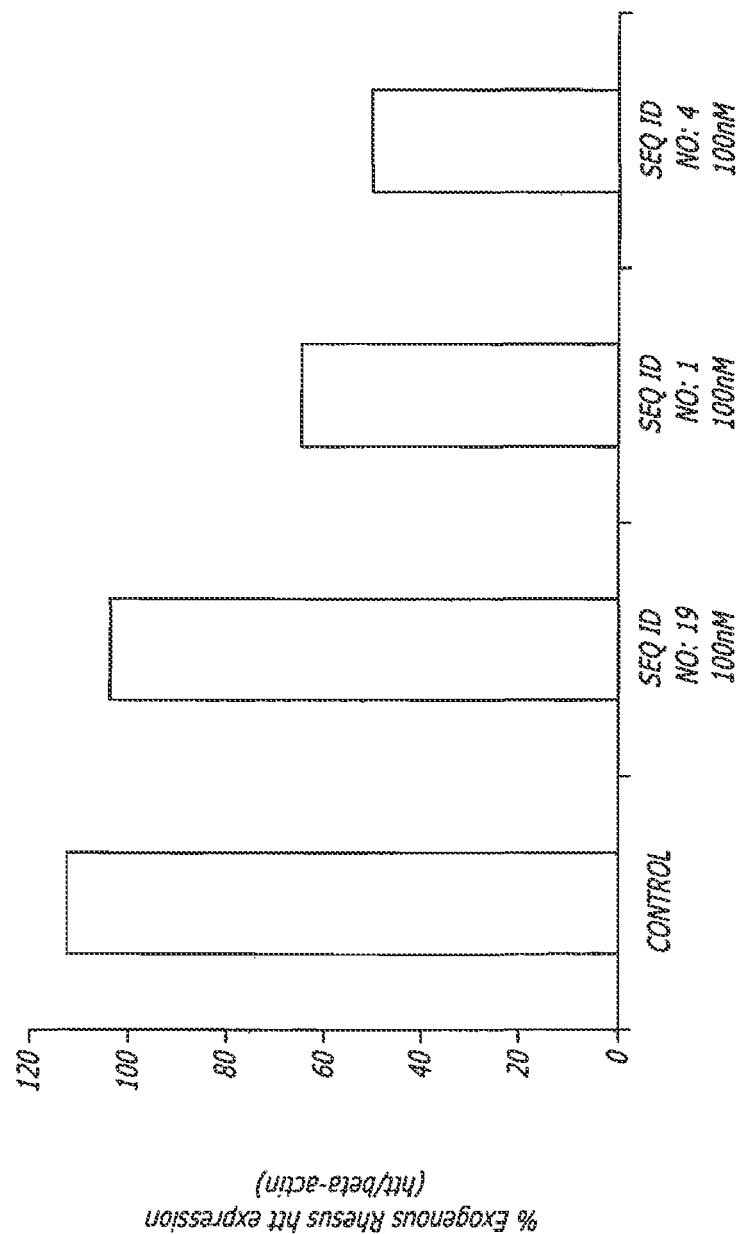

FIG. 13A
SEQ ID NO:20
5' ACCGGGAGTAGTCGTAATGTTATGCGAAGTGTTCAAGAGACACTTCGCATAAACATTACGACTACTCCTTTTTC 3'
3' CCTCATCAGCATTACAATACGCTTCACAAGTTCTCTGTGAAGCGTATTGTAATGCTGATGAGGAAAAAGACGT 5'

FIG. 13B
SEQ ID NO:21
5' ACCGGGAGTAGTCGTAATGTTATCTTCCTGTCAATAACATTACGACTACTCCTTTTTC 3'
3' CCTCATCAGCATTACAATAGAAGGACAGTTATTGTAATGCTGATGAGGAAAAAGACGT 5'

FIG. 13C
SEQ ID NO:22
5' ACCGGGAGTATTGTGGAACTTATTTCAAGAGAATAAGTTCCACAATACTCCTTTTTC 3'
3' CCTCATAACACCTTGAATAAAGTTCTCTTATTCAAGGTGTTATGAGGAAAAAGACGT 5'

FIG. 13D
SEQ ID NO:23

```
5' ACCGGGAGTATTGTGGAACTTATCTTCCCTGTCAATAAGTTCCACAATACTCCTTTTTC 3'
3'    CCTCATAACACCTTGAATAGAAGGACAGTTATTCAAGGTGTTATGAGGAAAAAGACGT 5'
```

FIG. 13E
SEQ ID NO:24

```
5' ACCGGGAGTATTGTGGAACTTATAGCTGGAGTTCAAGAGACTCCAGCTATAAGTTCCACAATACTCCTTTTTC 3'
3'    CCTCATAACACCTTGAATATCGACCTCAAGTTCTCTGAGGTCGATATTCAAGGTGTTATGAGGAAAAAGACGT 5'
```

FIG. 13F
SEQ ID NO:25

```
5' ACCGGGAGTATTGTGTGAACTTATAGCTGGAGCTTCCTGTCACTCCAGCTATAAGTTCCACAATACTCCTTTTTC 3'
3'    CCTCATAACACCCTTGAATATCGACCTCGAAGGACAGTGAGGTCGATATTCAAGGTGTTATGAGGAAAAAGACGT 5'
```

FIG. 18A
SEQ ID NO: 26

5' ACCGTGACGAGCAGTCGTTGATTAAATTCAAGAGATTTAATCAACACTGCTGTCATTTTTC 3'
3'     ACTGCTCGTCACAACTATTTAAGTTCTCTAAATAGTTGTGACGACAGTAAAAAGACGT 5'

FIG. 18B
SEQ ID NO: 27

5' ACCGTGACGAAGTCGTTGATTAAATTCAAGAGATTTAATCACGACTTCGTCATTTTTC 3'
3'     ACTGCTTCAGCACTAATTTAAGTTCTCTAAATTAGTGCTGAAGCAGTAAAAAGACGT 5'

METHODS AND SEQUENCES TO SUPPRESS PRIMATE HUNTINGTON GENE EXPRESSION

CROSS REFERENCE TO RELATED APPLICATIONS

This application is a Continuation of U.S. patent application Ser. No. 12/556,888, filed Sep. 10, 2009, now allowed, which was a Continuation of U.S. patent application Ser. No. 11/429,491, filed May 4, 2006, now abandoned, which claims priority under 35 U.S.C. §119(e) to U.S. Provisional Patent Application No. 60/678,729, filed May 6, 2005.

FIELD OF THE INVENTION

The present invention relates to inhibitory nucleic acid molecules that suppress the expression of the Huntington's disease gene in primates, including rhesus monkeys (*Macaca mulatto*) and humans (*Homo sapiens*).

BACKGROUND OF THE INVENTION

Huntington's disease ("HD") is a neurodegenerative brain disorder with a juvenile or adult onset. It slowly destroys an affected individual's ability to walk, think, talk and reason. Symptoms include changes in cognitive ability, such as impaired short-term memory and a decreased ability to concentrate; changes in mood, such as the development of mood swings, depression and irritability; and changes in coordination and physical movement such as clumsiness, involuntary movements and twitching. These symptoms gradually worsen until HD patients die, approximately 15-20 years after the onset of the disease.

While the biochemical cause of HD is not yet fully understood, it is now known that HD is inherited as an autosomal dominant trait. This inheritance feature means that every individual who inherits a mutated (expanded) HD gene from either parent will develop the disease.

One breakthrough in research regarding HD has been the identification of the mutated gene that causes HD. Based on this breakthrough, researchers and physicians now can predict which individuals will develop HD. Specifically, researchers and physicians can predict which individuals will develop HD by counting the number of "CAG repeats" that exist within a given individual's HD gene. If a person has 35 or fewer CAG repeats in both of their HD genes, that person will not develop HD. If a person has more than 35 CAG repeats in either of their HD genes, that person will develop the disease. The more CAG repeats a person has over 35, the earlier the person will develop the symptoms of HD.

The HD gene encodes for a protein called "huntingtin" (also known as "htt"). The exact function of huntingtin is not known. The expression of a mutant, expanded huntingtin protein is known to be the cause of HD, however. Some of the evidence that has led scientists to this conclusion includes mouse studies showing that the introduction of an expanded HD transgene in the mouse leads to the pathological and behavioral features of HD and its removal can resolve these effects. Thus, suppressing the production of huntingtin in brain cells may prevent or alleviate the symptoms or occurrence of HD.

Recent developments in genetic technologies have made the selective suppression of certain proteins, such as huntingtin, possible. Some background in the art is required to understand the potential impact of these technologies. Generally, for a protein to exert an effect, the cell that will use the protein must create it. To create a protein the cell first makes a copy of the protein's gene sequence in the nucleus of the cell. This copy of the gene sequence that encodes for the protein (called messenger RNA ("mRNA")) leaves the nucleus and is trafficked to a region of the cell containing ribosomes. Ribosomes read the sequence of the mRNA and create the protein for which it encodes. This process of new protein synthesis is known as translation. A variety of factors affect the rate and efficiency of protein translation. Among the most significant of these factors is the intrinsic stability of the mRNA itself. If the mRNA is degraded quickly within the cell (such as before it reaches a ribosome), it is unable to serve as a template for new protein translation, thus reducing the cell's ability to create the protein for which it encoded.

Based on the foregoing, the technology of RNA interference ("RNAi") has emerged. RNA interference is, in fact, a naturally-occurring mechanism for suppressing gene expression and subsequent protein translation. RNA interference suppresses protein translation by either degrading the mRNA before it can be translated or by binding the mRNA and directly preventing its translation. This naturally-occurring mechanism of RNA interference can also be artificially induced to occur in cells. For example, RNA interference can be achieved by introducing into cells short, double-stranded nucleic acid oligonucleotides corresponding to the mRNA for the gene to be suppressed, or by introducing into cells a sequence of DNA that encodes for a short, hairpin transcript of nucleic acids that folds back upon itself and forms a short, double-stranded nucleic acid oligonucleotide following further processing in the cell. This technology provides a means to suppress the expression of huntingtin in cells. The suppression of huntingtin in cells can be useful in the study of HD pathogenesis. Suppressing huntingtin in a patient also could prevent or alleviate the symptoms of HD.

SUMMARY OF THE INVENTION

The present invention describes methods, nucleic acid sequences and molecules, expression cassettes, and vectors for using RNA interference ("RNAi") to suppress expression of the HD gene. Suppressing expression of the HD gene can reduce levels of huntingtin within cells. This suppression and reduction can be useful in the study of HD pathogenesis. This suppression and reduction also can be useful in the prevention and treatment of the symptoms of HD. Specifically, RNAi is mediated by double stranded RNA ("dsRNA"), short hairpin RNA ("shRNA") or other nucleic acid molecules with similar characteristics. These nucleic acid molecules are processed or cut into smaller pieces by cellular enzymes including Dicer and Drosha. The smaller fragments of the nucleic acid molecules can then be taken up by a protein complex called the RNA-induced silencing complex ("RISC complex") that mediates degradation of mRNAs. The RISC complex will degrade mRNA that complementarily base pairs with the nucleic acid molecules it has taken up. In this manner, the mRNA is specifically destroyed, thus preventing the protein for which the mRNA encoded from being made.

The understanding of the mechanism of RNAi now allows geneticists to create nucleic acid molecules with sequences that are homologous to known gene sequences in order to suppress the expression or formation of certain proteins within a cell. In this invention, nucleic acid sequences and molecules that are homologous to primate HD mRNA sequences are introduced into cells to suppress expression of huntingtin protein. These nucleic acid sequences and molecules specifically suppress the expression of mRNA sequences that encode for primate huntingtin protein, including rhesus monkey and human huntingtin. Suppressing expression of this protein can be useful in the study of HD pathogenesis. This suppression also could be useful in the prevention and/or treatment of HD.

In one embodiment of the present invention, the invention includes a nucleic acid molecule comprising a first strand and a second strand wherein the first strand comprises a nucleotide sequence and wherein the second strand comprises the reverse complement of said first strand and wherein the nucleic acid molecule suppresses the expression of both *Macaca mulatto* and *Homo sapiens* mRNA sequences that encode for huntingtin.

In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 1 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 119 contiguous nucleotides encoded by SEQ ID NO: 2 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 3 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 4 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 5 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 6 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 7 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 119 contiguous nucleotides encoded by SEQ ID NO: 8 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 9 and wherein the second strand is complementary to at least 115 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 10 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 11 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 12 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ ID NO: 14 and wherein the second strand is complementary to at least 15 contiguous nucleotides of the first strand. In another embodiment of the present invention, the invention includes an isolated nucleic acid duplex comprising a first strand of nucleic acid and a second strand of nucleic acid, wherein the first strand comprises at least 19 contiguous nucleotides encoded by SEQ NO: 15 and wherein the second strand is complementary to at least 15 contiguous nucleotides of the first strand.

In another embodiment of the present invention, the invention includes an isolated nucleic acid duplex comprising a first strand of nucleic acid and a second strand of nucleic acid, wherein the first strand comprises at least 27 contiguous nucleotides encoded by SEQ ID NO: 9 and wherein the second strand is complementary to at least 23 contiguous nucleotides of the first strand. In another embodiment of the present invention, the invention includes an isolated nucleic acid duplex comprising a first strand of nucleic acid and a second strand of nucleic acid, wherein the first strand comprises at least 27 contiguous nucleotides encoded by SEQ ID NO: 10 and wherein the second strand is complementary to at least 23 contiguous nucleotides of the first strand. In another embodiment of the present invention, the invention includes an isolated nucleic acid duplex comprising a first strand of nucleic acid and a second strand of nucleic acid, wherein the first strand comprises at least 27 contiguous nucleotides encoded by SEQ ID NO: 11 and wherein the second strand is complementary to at least 23 contiguous nucleotides of the first strand. In another embodiment of the present invention, the invention includes an isolated nucleic acid duplex comprising a first strand of nucleic acid and a second strand of nucleic acid, wherein the first strand comprises at least 27 contiguous nucleotides encoded by SEQ ID NO: 12 and wherein the second strand is complementary to at least 23 contiguous nucleotides of the first strand. In another embodiment of the present invention, the invention includes an isolated nucleic acid duplex comprising a first strand of nucleic acid and a second strand of nucleic acid, wherein the first strand comprises at least 27 contiguous nucleotides encoded by SEQ ID NO: 13 and wherein the second strand is complementary to at least 23 contiguous nucleotides of the first strand, in another embodiment of the present invention, the invention includes an isolated nucleic acid duplex comprising a first strand of nucleic acid and a second strand of nucleic acid, wherein the first strand comprises at least 27 contiguous nucleotides encoded by SEQ ID NO: 14 and wherein the second strand is complementary to at least 23 contiguous nucleotides of the first strand. In another embodiment of the present invention, the invention includes an isolated nucleic acid duplex comprising a first strand of nucleic acid and a second strand of nucleic acid, wherein the first strand comprises at least 27 contiguous nucleotides encoded by SEQ ID NO: 15 and wherein the second strand is complementary to at least 23 contiguous nucleotides of the first strand.

In one embodiment of the present invention, the nucleic acid duplex is between 19 and 30 base pairs in length.

In another embodiment of the present invention, the first and/or second strand of the nucleic acid duplex comprises an overhang region. In another embodiment of the present invention, the first and/or second strand of the nucleic acid duplex comprises a 3' overhang region, a 5' overhang region, or both 3' and 5' overhang regions. In another embodiment of the present invention, the first and/or second strand of the nucleic acid duplex comprises an overhang region that is from approximately 1 to approximately 10 nucleotides in length.

In another embodiment of the present invention, the first and second strand of the nucleic acid duplex are operably linked by means of a nucleic acid loop strand that forms a hairpin structure comprising a duplex structure and a loop structure. In another embodiment of the present invention, the first and second strand of the nucleic acid duplex are operably linked by means of a nucleic acid loop that contains from 4 to 10 nucleotides.

In another embodiment of the present invention, the invention includes an expression cassette. In one embodiment, the expression cassette comprises a nucleic acid sequence encoding SEQ ID NO: 1. In another embodiment, the expression cassette comprises a nucleic acid sequence encoding SEQ ID NO: 2. In another embodiment, the expression cassette comprises a nucleic acid sequence encoding SEQ ID NO: 3. In another embodiment, the expression cassette comprises a nucleic acid sequence encoding SEQ ID NO: 4. In another embodiment, the expression cassette comprises a nucleic acid sequence encoding SEQ ID NO: 5. In another embodiment, the expression cassette comprises a nucleic acid sequence encoding SEQ ID NO: 6. In another embodiment, the expression cassette comprises a nucleic acid sequence encoding SEQ ID NO: 7. In another embodiment, the expression cassette comprises a nucleic acid sequence encoding SEQ ID NO: 8. In another embodiment, the expression cassette comprises a nucleic acid sequence encoding SEQ ID NO: 9. In another embodiment, the expression cassette comprises a nucleic acid sequence encoding SEQ ID NO: 10. In another embodiment, the expression cassette comprises a nucleic acid sequence encoding SEQ ID NO: 11. In another embodiment, the expression cassette comprises a nucleic acid sequence encoding SEQ ID NO: 12. In another embodiment, the expression cassette comprises a nucleic acid sequence encoding SEQ ID NO: 13. In another embodiment, the expression cassette comprises a nucleic acid sequence encoding SEQ ID NO: 14. In another embodiment, the expression cassette comprises a nucleic acid sequence encoding SEQ ID NO: 15.

In one embodiment of the present invention, the expression cassette also comprises a promoter. In another embodiment of the present invention, the expression cassette comprises a regulatable promoter. In another embodiment of the present invention, the expression cassette comprises a constitutive promoter. In another embodiment of the present invention, the expression cassette comprises a promoter that is a cytomegalovirus ("CMV") promoter. In another embodiment of the present invention, the expression cassette comprises a promoter that is a Rous sarcoma virus ("RSV") promoter. In another embodiment of the present invention, the expression cassette comprises a promoter utilized by RNA polymerase II. In another embodiment of the present invention, the expression cassette comprises a promoter utilized by RNA polymerase III.

In one embodiment of the present invention, the expression cassette comprises a polyadenylation signal. In another embodiment of the present invention, the expression cassette comprises a polyadenylation signal that is a synthetic minimal polyadenylation signal. In another embodiment of the present invention, the expression cassette comprises a marker gene.

In one embodiment of the present invention, the invention includes a vector comprising one or more of the expression cassettes previously described. In another embodiment of the present invention, the vector comprises a first and a second expression cassette.

In one embodiment, the first expression cassette of the vector encodes a nucleotide sequence encoding for SEQ ID NO. 1 and the second expression cassette of the vector encodes for a nucleotide sequence that is complementary to at least 15 contiguous nucleotides of SEQ ID. NO. 1. In another embodiment, the first expression cassette of the vector encodes a nucleotide sequence encoding for SEQ ID NO. 2 and the second expression cassette of the vector encodes for a nucleotide sequence that is complementary to at least 15 contiguous nucleotides of SEQ ID. NO. 2. In another embodiment, the first expression cassette of the vector encodes a nucleotide sequence encoding for SEQ ID NO. 3 and the second expression cassette of the vector encodes for a nucleotide sequence that is complementary to at least 15 contiguous nucleotides of SEQ ID NO. 3. In another embodiment, the first expression cassette of the vector encodes a nucleotide sequence encoding for SEQ ID NO. 4 and the second expression cassette of the vector encodes for a nucleotide sequence that is complementary to at least 15 contiguous nucleotides of SEQ ID. NO. 4. In another embodiment, the first expression cassette of the vector encodes a nucleotide sequence encoding for SEQ ID NO. 5 and the second expression cassette of the vector encodes for a nucleotide sequence that is complementary to at least 15 contiguous nucleotides of SEQ ID. NO. 5. In another embodiment, the first expression cassette of the vector encodes a nucleotide sequence encoding for SEQ ID NO. 6 and the second expression cassette of the vector encodes for a nucleotide sequence that is complementary to at least 15 contiguous nucleotides of SEQ ID. NO. 6. In another embodiment, the first expression cassette of the vector encodes a nucleotide sequence encoding for SEQ ID NO. 7 and the second expression cassette of the vector encodes for a nucleotide sequence that is complementary to at least 15 contiguous nucleotides of SEQ ID. NO. 7. In another embodiment, the first expression cassette of the vector encodes a nucleotide sequence encoding for SEQ ID NO. 8 and the second expression cassette of the vector encodes for a nucleotide sequence that is complementary to at least 15 contiguous nucleotides of SEQ ID, NO. 8. In another embodiment, the first expression cassette of the vector encodes a nucleotide sequence encoding for SEQ ID NO. 9 and the second expression cassette of the vector encodes for a nucleotide sequence that is complementary to at least 15 contiguous nucleotides of SEQ ID. NO. 9. In another embodiment, the first expression cassette of the vector encodes a nucleotide sequence encoding for SEQ ID NO. 10 and the second expression cassette of the vector encodes for a nucleotide sequence that is complementary to at least 15 contiguous nucleotides of SEQ ID. NO. 10. In another embodiment, the first expression cassette of the vector encodes a nucleotide sequence encoding for SEQ ID NO. 11 and the second expression cassette of the vector encodes for a nucleotide sequence that is complementary to at least 15 contiguous nucleotides of SEQ ID. NO. 1. In another embodiment, the first expression cassette of the vector encodes a nucleotide sequence encoding for SEQ ID NO. 12 and the second expression cassette of the vector encodes for a nucleotide sequence that is complementary to at least 15 contiguous nucleotides of SEQ ID. NO. 12. In another embodiment, the first expression cassette of the vector encodes a nucleotide sequence encoding for SEQ ID NO. 13 and the second expression cassette of the vector encodes for a nucleotide sequence that is complementary to at least 15 contiguous nucleotides of SEQ ID. NO. 13. In another embodiment, the first expression cassette of the vector encodes a nucleotide sequence encoding for SEQ ID NO. 14 and the second expression cassette of the vector encodes or a nucleotide sequence that is complementary to at least 15 contiguous nucleotides of SEQ ID. NO. 14. In another embodiment, the first expression cassette of the vector encodes a nucleotide sequence encoding for SEQ ID NO. 15 and the second expression cassette of the vector encodes for a nucleotide sequence that is complementary to at least 15 contiguous nucleotides of SEQ ID. NO. 15.

In another embodiment, the first expression cassette of the vector encodes a nucleotide sequence encoding for SEQ ID NO. 9 and the second expression cassette of the vector encodes for a nucleotide sequence that is complementary to at least 23 contiguous nucleotides of SEQ ID. NO. 9. In another embodiment, the first expression cassette of the vector encodes a nucleotide sequence encoding for SEQ ID NO. 10 and the second expression cassette of the vector encodes for a nucleotide sequence that is complementary to at least 23 contiguous nucleotides of SEQ ID. NO. 10. In another embodiment, the first expression cassette of the vector encodes a nucleotide sequence encoding for SEQ ID NO. 11 and the second expression cassette of the vector encodes for a nucleotide sequence that is complementary to at least 23 contiguous nucleotides of SEQ ID. NO. 1. In another embodiment, the first expression cassette of the vector encodes a nucleotide sequence encoding for SEQ ID NO. 12 and the second expression cassette of the vector encodes for a nucleotide sequence that is complementary to at least 23 contiguous nucleotides of SEQ ID. NO. 12. In another embodiment, the first expression cassette of the vector encodes a nucleotide sequence encoding for SEQ ID NO. 13 and the second expression cassette of the vector encodes for a nucleotide sequence that is complementary to at least 23 contiguous nucleotides of SEQ NO. 13. In another embodiment, the first expression cassette of the vector encodes a nucleotide sequence encoding for SEQ ID NO. 14 and the second expression cassette of the vector encodes for a nucleotide sequence that is complementary to at least 23 contiguous nucleotides of SEQ ID. NO. 14. In another embodiment, the first expression cassette of the vector encodes a nucleotide sequence encoding for SEQ ID NO. 15 and the second expression cassette of the vector encodes for a nucleotide sequence that is complementary to at least 23 contiguous nucleotides of SEQ ID. NO. 15.

In one embodiment of the present invention, the vector is a viral vector. In another embodiment of the present invention, the vector is an adenoviral virus vector. In another embodiment of the present invention, the vector is a lentiviral virus vector. In another embodiment of the present invention, the vector is an adeno-associated viral (AAV) virus vector.

In another embodiment of the present invention, the vector is a poliovirus vector. In another embodiment of the present invention, the vector is a herpes simplex virus vector. In another embodiment of the present invention, the vector is a feline immunodeficiency virus vector. In another embodiment of the present invention, the vector is a murine Maloney-based viral vector.

In another embodiment of the present invention, the vector comprises a promoter. In another embodiment of the present invention, the vector comprises an inducible promoter.

In one embodiment of the present invention, the invention includes a cell comprising a previously-described expression cassette. In another embodiment of the present invention, the cell is a mammalian cell. Another embodiment of the present invention includes a non-human mammal comprising a previously-described expression cassette.

The embodiments of the present invention also include methods. One method of the present invention includes a method of suppressing the accumulation of huntingtin in a cell comprising introducing a previously-described nucleic acid duplex into the cell in an amount sufficient to suppress accumulation of huntingtin in the cell. In another method of the present invention, accumulation of huntingtin is suppressed by at least 10%.

Another method of the present invention includes a method of preventing cytotoxic effects of mutant huntingtin in a cell comprising introducing a (previously-described nucleic acid duplex into the cell in an amount sufficient to suppress accumulation of the mutant huntingtin so that the nucleic acid duplex prevents cytotoxic effects of mutant huntingtin in the cell.

Another method of the present invention includes a method of inhibiting expression of a huntingtin gene in a cell comprising introducing a previously-described nucleic acid duplex into the cell in an amount sufficient to inhibit expression of huntingtin so that the nucleic acid duplex inhibits expression of huntingtin.

Another method of the present invention includes a method of inhibiting expression of huntingtin in *Macaca mulatto* and *Homo sapiens* comprising providing a *Macaca mulatto* or *Homo sapiens* containing a neuronal cell that contains and expresses the huntingtin gene and is susceptible to nucleic acid interference and contacting the *Macaca mulatto* or *Homo sapiens* with a previously-described nucleic acid duplex thereby inhibiting expression of the huntingtin gene. In another method of the present invention, expression of huntingtin is inhibited by at least 10%.

Another method of the present invention includes a method of preventing cytotoxic effects of Huntington's disease ("HD") in a *Macaca mulatto* or *Homo sapiens* comprising introducing a previously-described vector into a cell in an amount sufficient to suppress accumulation of a protein associated with HD, so that the resulting nucleic acid duplex prevents the cytotoxic effects of HD.

Another method of the present invention includes a method of inhibiting expression of the huntingtin gene in a *Macaca mulatto* or *Homo sapiens* comprising introducing a previously-described vector into a cell in an amount sufficient to inhibit expression of the huntingtin gene so that the resulting nucleic acid duplex inhibits expression of the huntingtin protein.

Another method of the present invention includes a method of inhibiting expression of huntingtin in a *Macaca mulatto* or *Homo sapiens* comprising providing a *Macaca mulatto* or *Homo sapiens* containing a neuronal cell, wherein the neuronal cell contains and expresses the huntingtin gene and is susceptible to nucleic acid interference, and contacting the *Macaca mulatto* or *Homo sapiens* with a previously-described vector, thereby inhibiting expression of the huntingtin gene.

In one embodiment of the present invention, the nucleic acid duplexes or vectors are administered to the intrathecal space of the spinal cord. In another embodiment of the present invention, the nucleic acid duplexes or vectors are administered to the cerebrospinal fluid in one or more of the cerebral ventricles of the brain. In another embodiment of the present invention, the nucleic acid duplexes or vectors are administered directly into the brain tissue of the cerebral cortex. In another embodiment of the methods of the present invention, the nucleic acid duplexes or vectors are administered locally to the basal ganglia. In another embodiment of the present invention, the nucleic acid duplexes or vectors are administered specifically to the caudate nucleus and the putamen.

BRIEF DESCRIPTION OF THE FIGURES

FIGS. 8A-8D show suppression of the endogenous human HD gene at 4 different siNA doses in HeLa cells.

FIG. 9 shows suppression of exogenous rhesus huntingtin protein expression in LLC-MK2 cells.

FIGS. 13A-F show additional shNA sequences used in embodiments according to the present invention.

FIGS. 18A-B show additional shNA sequences used in embodiments according to the present invention.

DETAILED DESCRIPTION OF THE INVENTION

Figure 1:
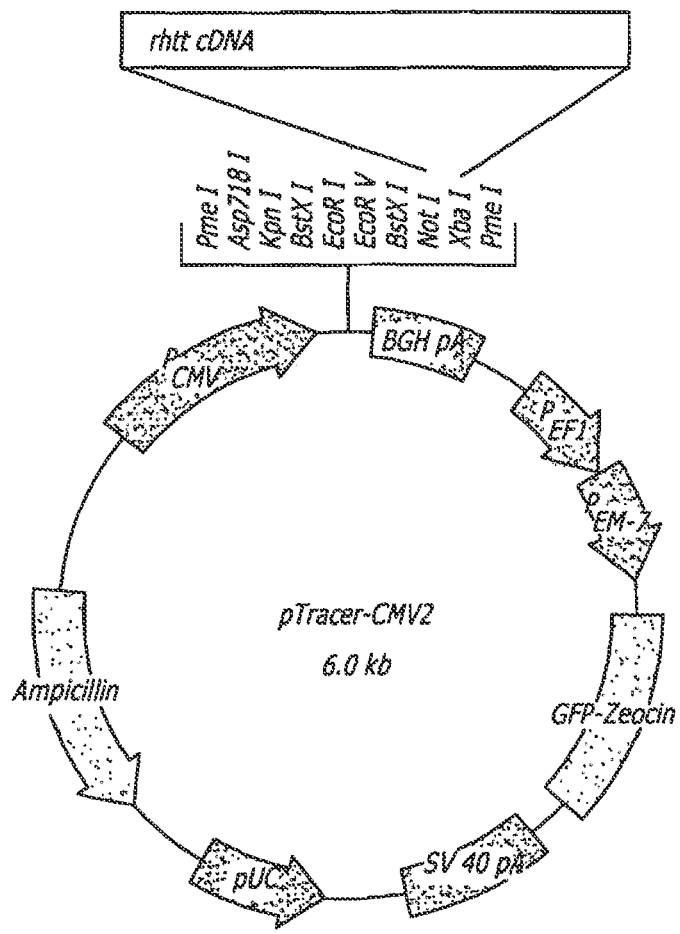
FIG. 1 shows a target plasmid for nucleic acid sequence characterization in HEK293 cells.

The term "SEQ ID NO: X" (where X is any number from 1 to 15) refers to, in one embodiment, each number's sequence as defined in Table 1 (identified sequence). SEQ ID NO: X must also be read to encompass sequences that would hybridize with the complementary strand of a sequence set forth in SEQ ID NOS: 1-15 and reduce the particular SEQ ID NO:'s target mRNA in a cell type selected from, without limitation, HEK293 cells, 4 MBR5 cells, LLC-MK2 cells, HeLA cells or any other *Macaca mulatto* or *Homo sapien* cell type. Under this definition, claimed sequences can include at least 99% sequence homology with the identified sequence; at least 98% sequence homology with the identified sequence; at least 95% sequence homology with the identified sequence; at least 90% sequence homology with the identified sequence; or at least 85% sequence homology with the identified sequence.

The terms "nucleic acid" or "nucleic acid molecules" refer to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof. The nucleic acid molecules of the present invention can include any type of nucleic acid molecule capable of mediating RNA interference, such as, without limitation, short interfering nucleic acid (siNA), short hairpin nucleic acid (shNA), short interfering RNA (siRNA), short hairpin RNA (shRNA), micro-RNA (miRNA), and double-stranded RNA (dsRNA). The nucleic acid molecules of the present invention also include similar DNA sequences. Further, the nucleic acid and nucleic acid molecules of the present invention can contain unmodified or modified nucleotides. Modified nucleotides refer to nucleotides which contain a modification in the chemical structure of a nucleotide base, sugar and/or phosphate. Such modifications can be made to improve the stability and/or efficacy of nucleic acid molecules and are described in patents and publications such as U.S. Pat. No. 6,617,438, U.S. Pat. No. 5,334,711; U.S. Pat. No. 5,716,824; U.S. Pat. No. 5,627,053; U.S. Provisional Patent Application No. 60/082,404, International Patent Cooperation Treaty Publication Number ("PCTPN") WO 98/13526; PCTPN WO 92/07065; PCTPN WO 03/070897; PCTPN WO 97/26270; PCTPN WO 93/15187; Beigelman et al., 1995, J. Biol. Chem., 270, 25702; Usman and Cedergren, 1992, TIBS. 17, 34; Usman et al., 1994, Nucleic Acids Syrup. Ser. 31, 163; Burgin et al., 1996, Biochemistry, 35, 14090; Perrault et al. Nature, 1990, 344, 565-568; Pieken et al. Science, 1991, 253, 314-317; Usman and Cedergren, Trends in Biochem. Sci., 1992, 17, 334-339; Karpeisky et al., 1998, Tetrahedron Lett, 39, 1131; Earnshaw and Gait, 1998, Biopolymers (Nucleic Acid Sciences), 48, 39-55; Verma and Eckstein, 1998, Annu Rev. Biochem., 67, 99-134; Burlina et al., 1997, Bioorg. Med. Chem., 5, 1999-2010; Limbach et al., 1994, Nucleic Acids Res. 22, 2183; and Burgin et al., 1996, Biochemistry, 35, 14090. Such patents and publications describe general methods and strategies to modify nucleic acid molecules and are incorporated by reference herein.

The phrase "expression cassette" as used herein means a nucleic acid sequence capable of directing expression of a particular nucleotide sequence in an appropriate host cell, with additional sequences that facilitate appropriate transcription of the nucleic acid sequence of interest, in addition to the nucleotide sequence of interest, the expression cassette can include a promoter operably linked to the nucleotide sequence of interest that also can be operably linked to termination signals. The expression cassette also can include expression enhancers. The expression cassette including the nucleotide sequence of interest can be chimeric. The expression cassette also can be one that is naturally occurring but has been obtained in a recombinant form useful for heterologous expression. The expression of the nucleotide sequence in the expression cassette can be under the control of a constitutive promoter or of a regulatable promoter that initiates transcription only when the host cell is exposed to some particular stimulus. In the case of a multicellular organism, the promoter also can be specific to a particular tissue or organ or stage of development.

The term "promoter" refers to a nucleotide sequence, usually upstream (5 prime) of the nucleotide sequence of interest, which directs and/or controls expression of the nucleotide sequence of interest by providing for recognition by RNA polymerase and other factors required for proper transcription. As used herein, the term "promoter" includes (but is not limited to) a minimal promoter that is a short DNA sequence comprised of a TATA-box and other sequences that serve to specify the site of transcription initiation, to which regulatory elements are added for control of expression. The term "promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. The term "enhancer" refers to a DNA sequence that can stimulate promoter activity and can be an innate element of the promoter or a heterologous element inserted to enhance the level or tissue specificity of a promoter. Enhancers are capable of operating in both orientations (normal or flipped), and are capable of functioning even when moved either upstream or downstream of the promoter. Both enhancers and other upstream promoter elements bind sequence-specific DNA-binding proteins that mediate their effects. Promoters can be derived in their entirety from a native gene, or be composed of different elements derived from different promoters found in nature, or even be comprised of synthetic DNA segments. A promoter also can contain DNA sequences that are involved in the binding of protein factors that control the effectiveness of transcription initiation in response to physiological or developmental conditions. Specific promoters used in accordance with the present invention can include, for example and without limitation pol II promoters (including, without limitation cytomegalovirus ("CMV") promoters, chicken .beta.-actin ("CBA") promoters, Rous sarcoma virus ("RSV") promoters and neuron-specific enolase ("NSE") promoters). Furthermore, specific promoters used in accordance with the present invention can include, for example and without limitation, pol III promoters (including, without limitation, human H1 and human or murine U6 promoters, as well as H1 and U6 promoters engineered to be expressed in a regulated way such as described in United States Patent Published Application No 2005/0064489).

The term "vector" is defined to include any virus, as well as any plasmid, cosmid, phage, binary vector or segment of nucleic acid (DNA or RNA) in double or single stranded linear or circular form that may or may not be self transmissible or mobilizable, and that can transform eukaryotic host cells either by integration into the cellular genome or by existing extrachromosomally (e.g., autonomous replicating plasmid with an origin of replication).

The gene involved in Huntington's disease ("HD") (IT-15) is located on chromosome 4 at the end of the short arm. This gene encodes for the protein huntingtin (also known as "htt"). The mutation in the HD gene responsible for HD is an unstable expanded CAG trinucleotide repeat within the coding region of the gene. This mutation results in a huntingtin protein with an expanded glutamine sequence. While the normal and abnormal functions of huntingtin are not known, the presence of the mutated form of huntingtin has been correlated with the occurrence of HD symptoms. Further, the abnormal huntingtin protein appears to accumulate abnormally in neuronal nuclei. Thus, blocking the expression of huntingtin provides a useful mechanism to study HD pathogenesis and can also provide a potential treatment for HD. A proof-of-principle that suppressing the expression of mutant huntingtin protein can be therapeutic for HD has been shown in mice by Harper et al. who showed that suppression of a mutant HD transgene in mice by use of RNA interference resulted in improvements in the disease phenotype of the transgenic mice. Proceedings of the National Academy of Sciences, 2005, 102(16) 5820-5825. It should be noted, however, that the present invention differs from this prior art in that the shNA sequence used and disclosed by Harper et al. is different from any and all of the nucleic acid sequences of the present invention. Furthermore, Harper et al. does not indicate whether the nucleic acid sequence of their study is homologous with both rhesus and human HD genes, whereas the nucleic acid sequences of the present invention are known to be homologous with both rhesus (*Macaca mulatto*) and human (*Homo sapiens*) HD genes. Thus, one important benefit of the present invention is that the same nucleic acid sequences can be studied and characterized for toxicological and pharmacological properties and safety in the non-human primate *Macaca mulatto* and then, without alteration, can also be used for therapeutic benefit in *Homo sapiens*.

In order to use RNA interference ("RNAi") to suppress expression of rhesus and human huntingtin, it was first necessary to identify nucleic acid sequences that effectively suppress the expression of human and rhesus HD genes. Towards this goal, a PCR strategy was used to clone and assemble 3437 bp of the 5' portion of the rhesus HD gene. Briefly, a series of PCR primers predicted to anneal to the rhesus HD cDNA were designed based on evolutionarily conserved sequences identified in an alignment of the human (NM_002111) and pig (AB016793) cDNA sequences. These primers were used to amplify partially overlapping portions of the rhesus HD gene from first strand cDNA prepared from rhesus brain and kidney tissues (BioChain Institute, Inc; C1534035 and C1534142 respectively) using high fidelity DNA polymerases. The recovered PCR products were cloned into pCR-Blunt-TOPO (Invitrogen) and sequenced using standard methods. Sequence alignments between multiple, independently derived clones were analyzed to ensure the elimination of potential PCR and sequencing errors. This sequence information was also used to design additional primers to clone gaps in the recovered HD cDNA sequence. A single composite clone containing 3437 bp of the rhesus HD cDNA was assembled using PCR and conventional cloning techniques.

Next, potential synthetic nucleic acid suppressor sequences for rhesus monkey huntingtin that correspond with portions of the human sequence (i.e., target genes were rhesus and human HD genes) were identified using online software (http://www.dharmacon.com/) and also obtained from Dharmacon® (Dharmacon Research, Inc., Boulder, Colo.). These nucleic acid sequences included those in the following Table 1:

TABLE 1

| SEQ ID NO: | Nucleic Acid Name | Nucleotide Base Sequence | Position in human cDNA (NM_002111) |
|---|---|---|---|
| 1 | Rh#1-19 | TGACAGCAGTGTTGATAAA | 2071-2089 |
| 2 | rh#2-19 | AAGAACGAGTGCTCAATAA | 2862-2880 |
| 3 | Rh#4-19 | TTTATGAACTGACGTTACA | 1221-1239 |
| 4 | Rh#5-19 | GGAGTATTGTGGAACTTAT | 1405-1423 |
| 5 | Rh#6-19 | GAGTATTGTGGAACTTATA | 1405-1423 |
| 6 | Rh#11-19 | AGACCGTGTGAATCATTGT | 442-460 |
| 7 | Rh#12-19 | GGTTACAGCTCGAGCTCTA | 645-663 |
| 8 | Rh#13-19 | GGTTTTGTTAAAGGCCTTC | 898-916 |
| 9 | Rh#1-27 | TGACAGCAGTGTTGATAAATTTGTGTT | 2071-2097 |
| 10 | Rh#2-27 | AAGAACGAGTGCTCAATAATGTTGTCA | 2862-2888 |
| 11 | Rh#4-27 | TTTATGAACTGACGTTACATCATACAC | 1221-1247 |
| 12 | Rh#5-27 | GGAGTATTGTGGAACTTATAGCTGGAG | 1404-1430 |
| 13 | Rh#6-27 | GAGTATTGTGGAACTTATAGCTGGAGG | 1405-1431 |
| 14 | Rh#11-27 | AGACCGTGTGAATCATTGTCTGACAAT | 442-468 |
| 15 | Rh#13-27 | GGTTTTGTTAAAGGCCTTCATAGCGAA | 898-924 |

Note that, as will be understood by one of skill in the art, the nucleic acid molecules of the present invention include the sequences in the preceding table, the reverse complement of these sequences and RNA based sequences including uracils in the place of the listed thymines. Thus, the sequences in the preceding table can be considered target sequences as well as sequences included in the nucleic acid molecules of the present invention. SEQ ID NOS. 1-8 are 19 nucleotide base sequences. SEQ ID NO. 9-15 are the same sequences extended to 27 nucleotide base sequences. The sequence identified as SEQ ID NO. 7 was not extended into a 27 nucleotide base sequence because extending this sequence resulted in a mismatch between the rhesus monkey and human HD sequences. Control sequences also were chosen. The control sequences included a non-sense scrambled control (SEQ ID NO, 19; TAGCGACTAAACACATCAA) and a TNFα sequence (SEQ ID NO, 16; AATCCTCCTTCGTAT-TATA) both purchased from Dharmacon.

To identify which of the above identified 19 nucleotide nucleic acid sequences most effectively suppressed rhesus monkey huntingtin expression, an in vitro co-transfection assay system was developed. Referring to FIG. 1, rhesus monkey HD gene sequences were subcloned into pTracer™-CMV2 (Invitrogen, Corp., Carlsbad, Calif.) to generate pTracer-rhuntingtin (pTRACER-rhHD). The recombinant plasmid also included a GFP-Zeocin reporter gene for transfection efficiency normalization. The CMV promoter directed constitutive expression of the target gene (rhesus monkey HD) while the EF1 promoter directed constitutive expression of the GFP-Zeocin reporter gene.

The generated recombinant plasmids were used to facilitate screening of nucleic acid sequences by co-transfection into a eukaryotic cell line. Specifically, HEK293 cell cultures at 60-70% confluency were co-transfected with the appropriate target plasmid (2 µg/well of a 6-well plate) and test nucleic acid sequences (100 nM) directed against rhesus monkey HD. (SEQ ID NO: 1 through SEQ ID NO: 8), TNFα as a control (SEQ ID NO. 16) or a non-sense scrambled control (SEQ ID NO, 19). Forty-eight hours post-transfection, total cellular RNA was harvested from the cells and used to make cDNA by standard methods. The cDNAs were analyzed for target (RD) and reporter (GFP) gene expression levels using realtime PCR methods. The data was normalized for GFP expression levels to control for variation in transfection efficiency.

Figure 2:
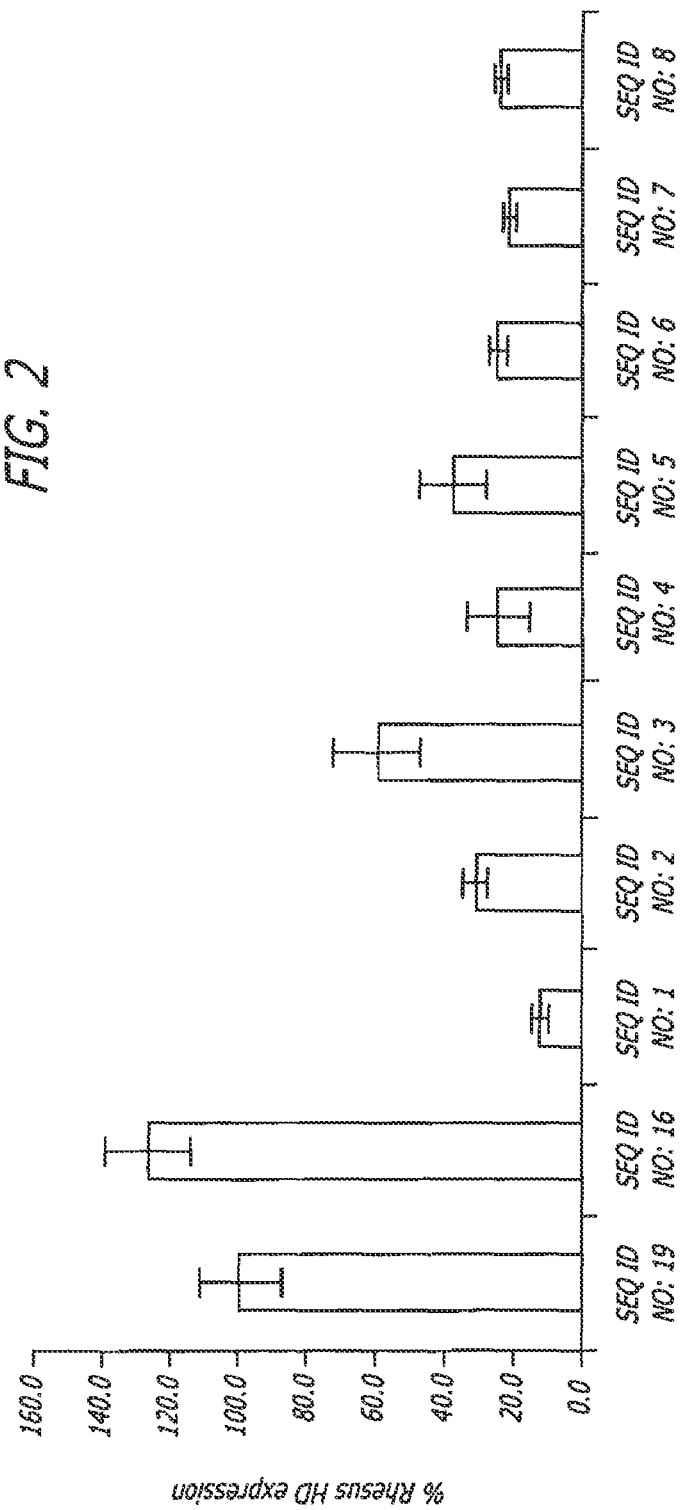
FIG. 2 shows rhesus monkey HD mRNA suppression by siNA sequences in vitro in HEK293 cells.

FIG. 2 shows the results of the rhesus monkey HD transfection studies related to each of the test nucleic acid sequence's ability to suppress rhesus monkey HD mRNA. As measured by realtime PCR, all non-control sequences effectively suppressed expression of the HD gene when compared to mock treated control cells (set at 100% expression). Because the nucleic acid sequences evaluated in the present experiment have complete sequence identity to portions of the human HD gene sequence, it is reasonable to expect that they also suppress the expression of the human HD gene, thus suppressing production of human huntingtin protein.

Figure 3:
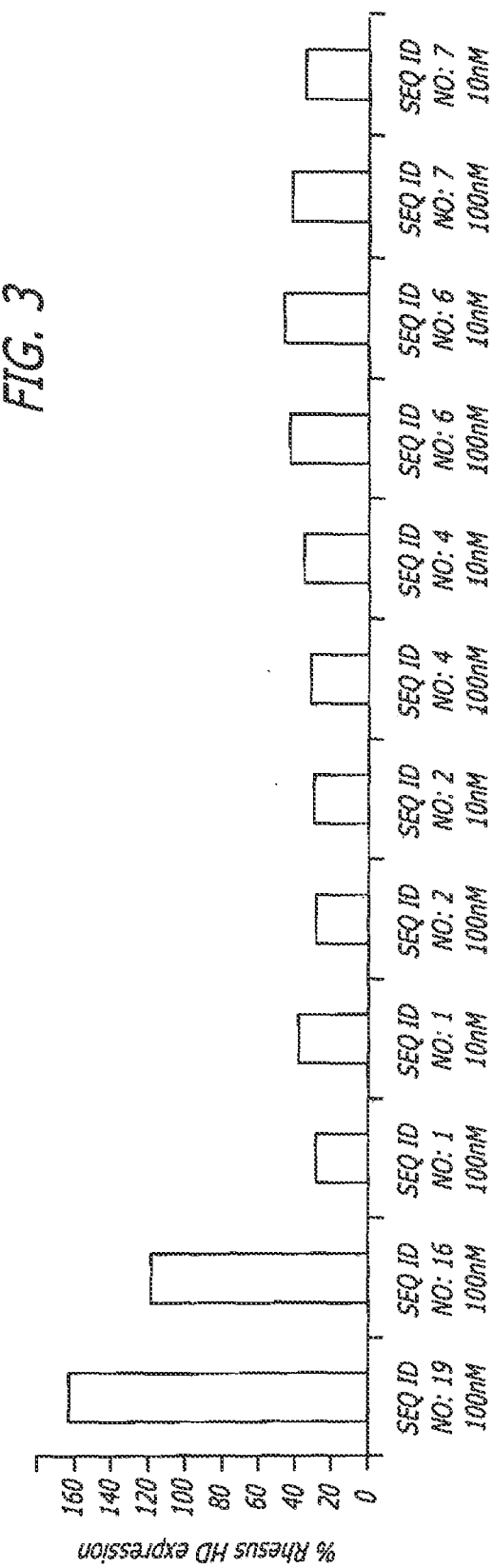
FIG. 3 shows suppression of the endogenous rhesus HD gene at two different siNA doses in 4 MBR5 cells.

Next, the ability of a subset of the 19 nucleotide sequences was evaluated for its ability to suppress expression of the endogenous rhesus HD gene at two different doses, 100 nM and 10 nM. Specifically, 4 MBr5 cell line cultures Obtained from American Type Culture Collection ("ATCC") (cells from a rhesus lung cell line) at 70-80% confluency were transfected with test nucleic acid sequences (SEQ ID NO: 1; SEQ ID NO: 2; SEQ ID NO: 4; SEQ ID NO: 6; and SEQ ID NO: 7) directed against rhesus HD mRNA at either 100 nM or 10 nM or control sequences (SEQ ID NO: 19 (scrambled) or SEQ ID NC): 16 (off-target TNFα control)) at 100 nM. Forty-eight hours post transfection total cellular RNA was collected from the cells and used to generate cDNA by standard methods. The cDNAs were used to analyze for rhesus HD and control gene expression using realtime PCR methods. A separate realtime PCR reaction was performed to assess the level of rhesus GAPDH expression. All of the expression data was normalized to GAPDH expression to allow the assessment of the efficacy of siNA-mediated knockdown of rhesus HD in the rhesus cell lines. As shown in FIG. 3, all sequences directed against rhesus HD mRNA suppressed rhesus HD gene expression at both doses when compared to controls.

Figure 4:
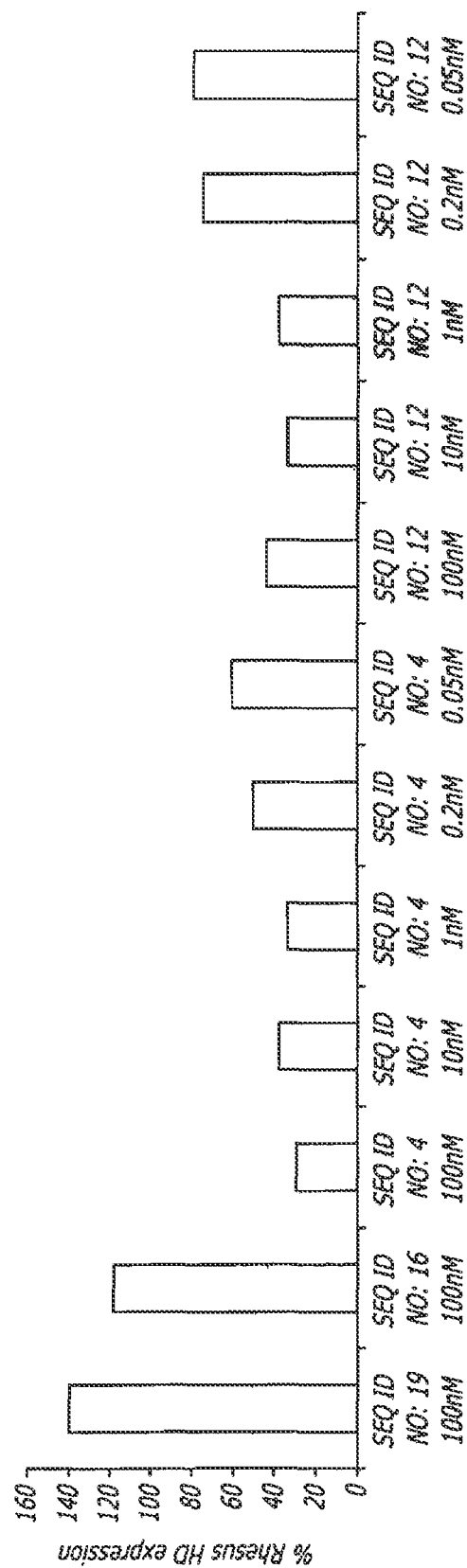
FIG. 4 shows suppression of the endogenous rhesus HD gene at five different siNA doses using both 19 and 27 nucleotide length siNAs in 4 MBR5 cells.

Next, an experiment was performed to evaluate the dependence of rhesus HD mRNA suppression on the length and dose of provided nucleic acid sequences. Specifically, 4 MBr5 cells were transfected as described above but with 100 nM, 110 nM, 1.0 nM, 0.2 nM or 0.05 nM of SEQ ID NO: 4 (19 nucleotide sequence); 100 nM, 10 nM, 1.0 nM, 0.2 nM or 0.05 nM of SEQ ID NO: 12 (corresponding 27 nucleotide sequence); 100 nM SEQ ID NO: 19 (scrambled) or 100 nM SEQ ID NO: 16 (off-target TNFα control). As shown in FIG. 4, all doses of both sequence lengths suppressed rhesus HD gene expression when compared to controls. While all doses were effective in 4 MBr5 cells, 100 nM, 10 nM and 1 nM were the most effective doses for suppressing rhesus HD gene expression regardless of sequence length.

Figure 5:
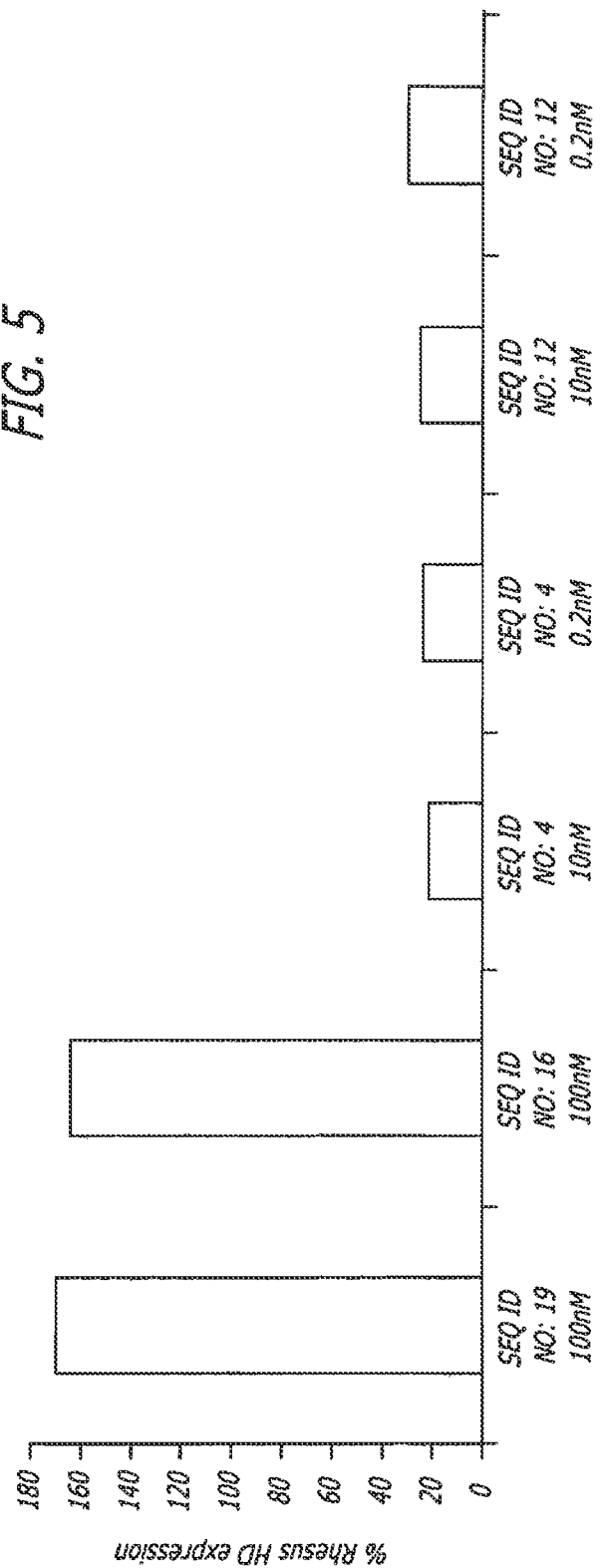
FIGS. 5 and 6 show suppression of the endogenous rhesus HD gene using both 19 and 27 nucleotide length siNAs in LLC-MK2 cells.

A subsequent experiment evaluating the siNA's ability to suppress expression of the endogenous rhesus HD gene also examined the effectiveness of a 27 nucleotide sequence as compared to its previously-evaluated 19 nucleotide sequence counterpart in LLC-MK2 cells. In this experiment, LLC-MK2 cells (a rhesus kidney cell line also obtained from ATCC) at 70-80% confluency were transfected with test nucleic acid sequences (SEQ ID NO: 4 and SEQ ID NO: δ 1.2) at one of two doses, 10 nM or 0.2 nM as well as controls (SEQ ID N): 19 and SEQ ID NO: 16) at 100 µM. Forty-eight hours post transfection total cellular RNA was collected from the cells and used to generate cDNA by standard methods. The cDNAs were used to analyze for rhesus HD and control gene expression using realtime PCR methods. A separate realtime PCR reaction was performed to assess the level of rhesus GAPDH expression. All of the expression data was normalized to GAPDH expression to allow the assessment of the efficacy of siNA-mediated knockdown of rhesus HD in the rhesus cell lines. As shown in FIG. 5, all sequences directed against rhesus HD mRNA suppressed rhesus HD gene expression at both doses when compared to controls.

Figure 6:
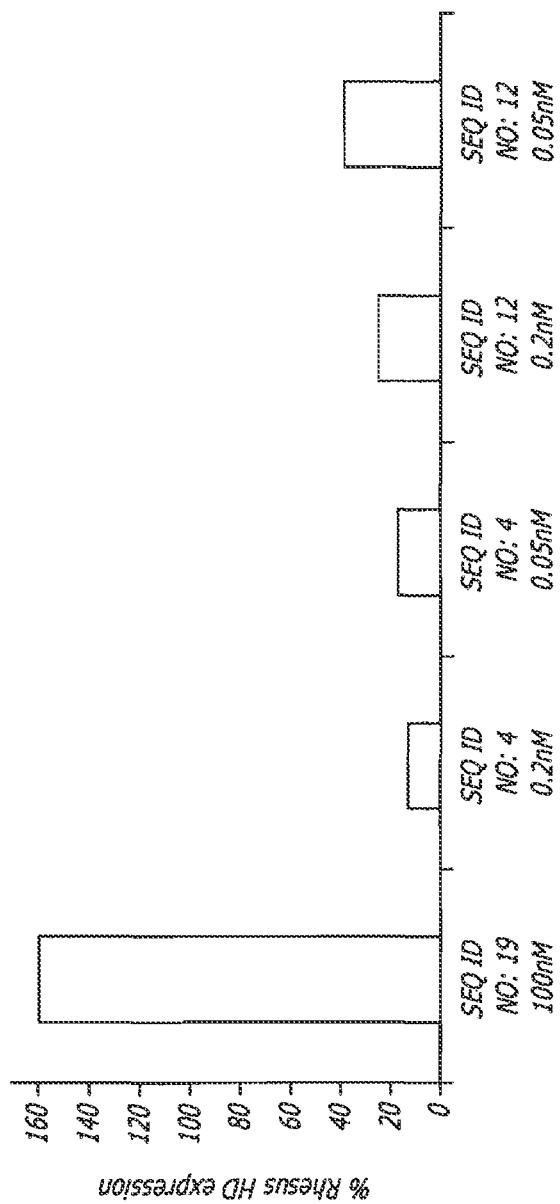

Following the experiment described in the preceding paragraph, an identical experiment was conducted with the exception that an additional lower dose of SEQ ID NOS: 4 and 12 (0.05 nM) was compared against the effectiveness of the 0.2 nM dose and control SEQ ID NO: 19 (100 nM). As shown in FIG. 6, all sequences and doses suppressed endogenous rhesus HD gene expression in LLC-MK2 cells.

Figure 7:
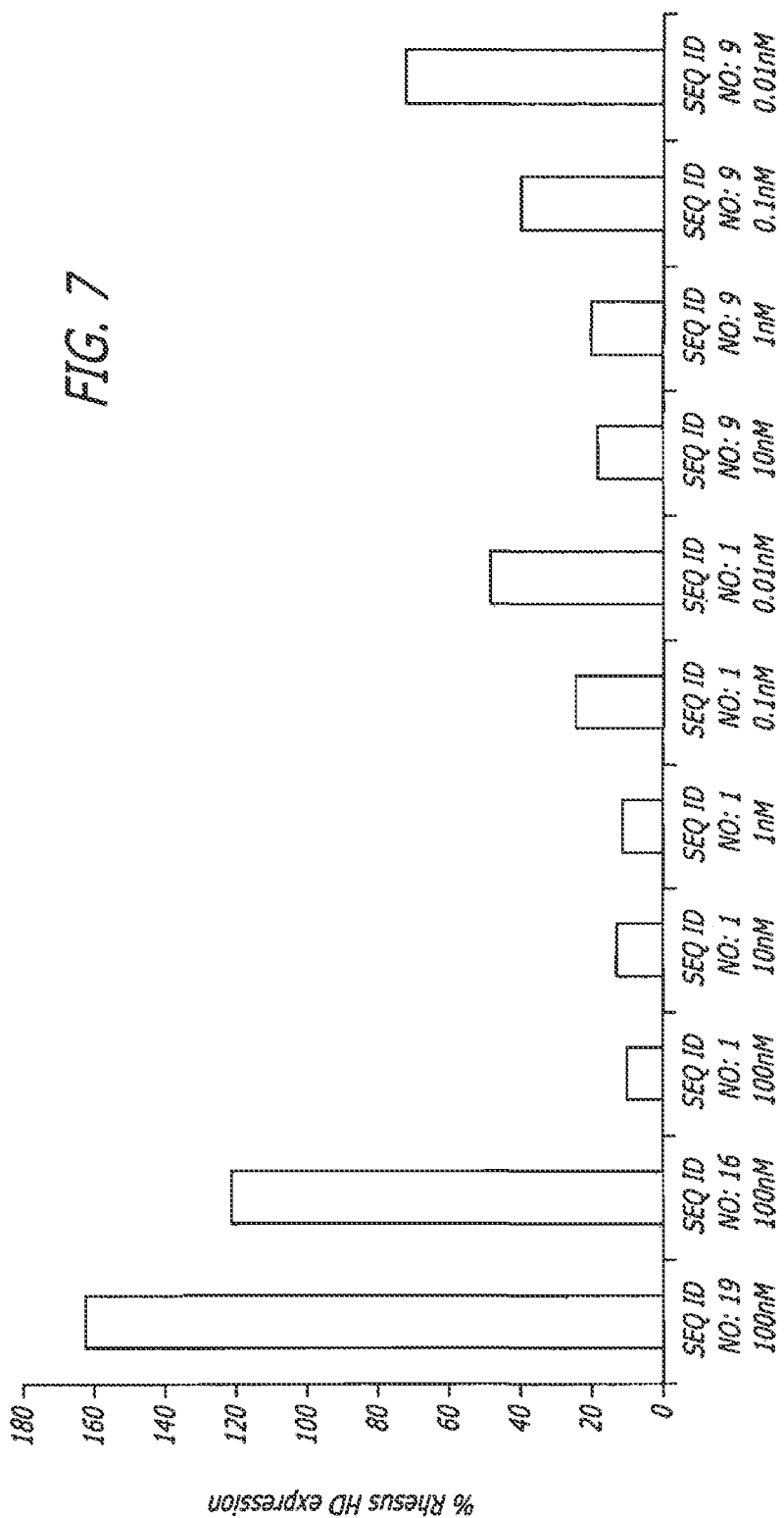
FIG. 7 also shows suppression of the endogenous rhesus HD gene using different doses of both 19 and 27 nucleotide length siNAs in LLC-MK2 cells.

The effectiveness of different sequence lengths and doses was also compared using SEQ ID NOS: 1 and 9. Following the same procedures used in the two previously described experiments, LLC-MK2 cells were transfected with 100 nM, 10 nM, 1 nM, 0.1 nM or 0.01 nM SEQ ID NO: 1 (19 nucleotide sequence); 10 nM, 1 nM, 0.1 nM or 0.01 nM SEQ ID NO: 9 (corresponding 27 nucleotide sequence); or control SEQ ID NOS: 19 or 16 (100 nM). As shown in FIG. 7, all doses of both sequences suppressed endogenous rhesus HD gene expression in LLC-MK2 cells with the 1 nM and higher doses of SEQ ID NOS: 1 and 9 providing the most suppression. In addition, from this experiment the IC50 (inhibitor concentration required for 50% suppression) values for these two siNAs are estimated to be 10 .mu.M and 75 .mu.M respectively.

Figure 8A:
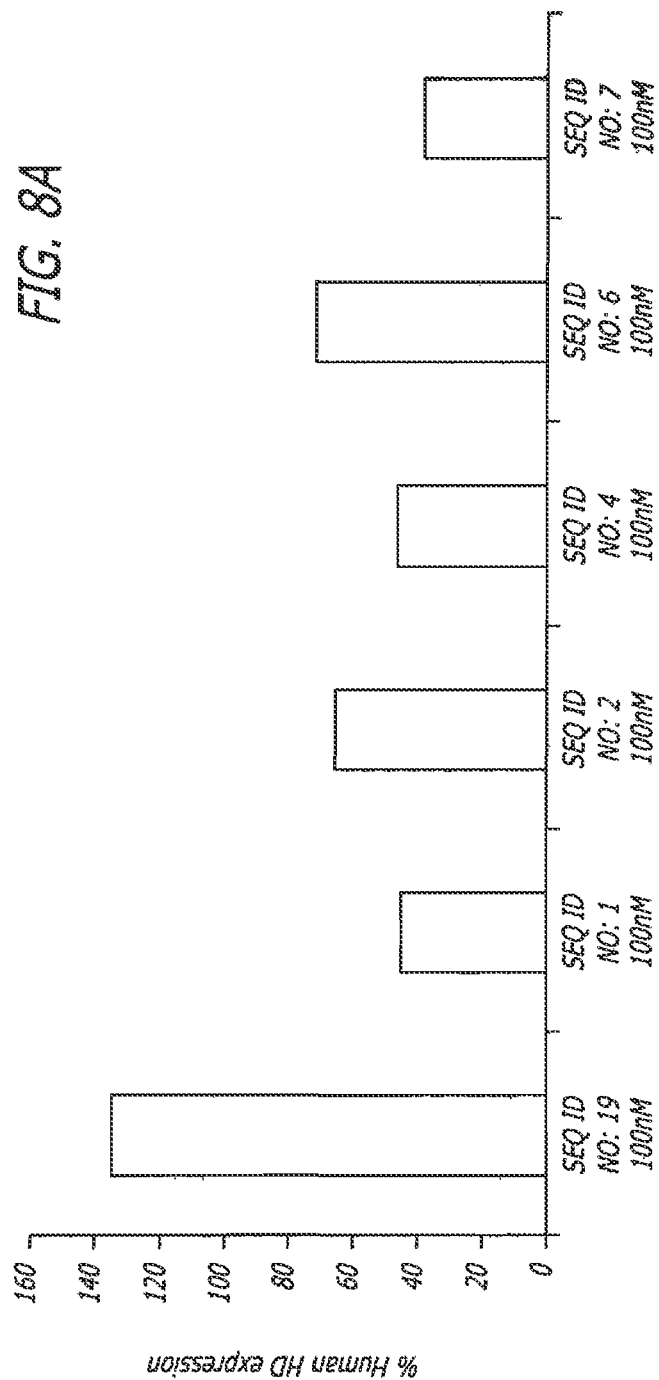

Next, a subset of the identified siNA sequences was tested for the chosen sequence's ability to suppress expression of the endogenous human HD gene. In this experiment, HeLa cells (obtained from ATCC) at 70-80% confluency were transfected with test nucleic acid sequences (SEQ ID NO: 1; SEQ ID NO: 2; SEQ ID NO: 4; SEQ ID NO: 6; or SEQ ID NO: 7) or control (SEQ ID NO: 19) at 100 nM. Forty-eight hours post transfection total cellular RNA was collected from the cells and used to generate cDNA by standard methods. The cDNAs were used to analyze for human HD and control gene expression using realtime PCR methods. A separate realtime PCR reaction was performed to assess the level of human GAPDH expression. All of the expression data was normalized to GAPDH expression to allow the assessment of the efficacy of siNA-mediated knockdown of human HD in the HeLa cell line. As shown in FIG. 8A, all sequences directed against human HD mRNA suppressed human HD gene expression when compared to controls.

The experiment just described was next repeated using doses of either 1 nM, 0.1 nM or 0.01 nM SEQ ID NOS. 1, 2, 4, 6 or 7 or 100 nM of control SEQ ID NO: 19. As shown in FIGS. 8B-8D, all doses of each of these SEQ ID NOS. 1, 2, 4, 6 and 7 were effective in suppressing endogenous human HD gene expression in HeLa cells. In only one instance was human HD suppression not observed, SEQ ID NO: 2 at the lowest dose (0.01 nM).

Following the previously described experiments, studies were undertaken to determine whether sequences of the present invention suppress exogenous huntingtin protein expression. In this first protein suppression experiment, suppression of the partial rhesus huntingtin protein expressed from the pTRACER plasmid depicted in FIG. 1 was measured by western blot analysis. Specifically, LLC-MK2 cells were cotransfected with the pTRACER-rhHD plasmid (2 µg/well of a 6-well plate) and 100 nM of either SEQ ID NO: 19 (control); SEQ ID NO: 1 or SEQ ID NO: 4. Controls in this experiment also consisted of LLC-MK2 cells transfected solely with the pTRACER-rhID plasmid. Protein was harvested 48 hours post-transfection and was analyzed using western blot analysis. In this analysis, 10 µg of total protein was loaded per well. Rhesus huntingtin protein expression was measured using the Chemicon® International (Temecula, Calif.) huntingtin antibody MAB2168 and β-actin was measured with Abcam® (Cambridge, Mass.) antibody 20272-100. To quantify huntingtin protein expression the intensities of the bands for huntingtin and .beta.-actin on the autoradiogram of the western blot were measured by densitometry. Huntingtin protein expression was normalized to β-actin expression. As can be seen in FIG. 9, both SEQ ID NO: and SEQ ID NO: 4 were effective to suppress exogenous huntingtin protein expression when compared to controls transfected with the pTRACER-rhHD plasmid and SEQ ID NO: 19 or the pTRACER-rhHD plasmid alone.

Figure 10:
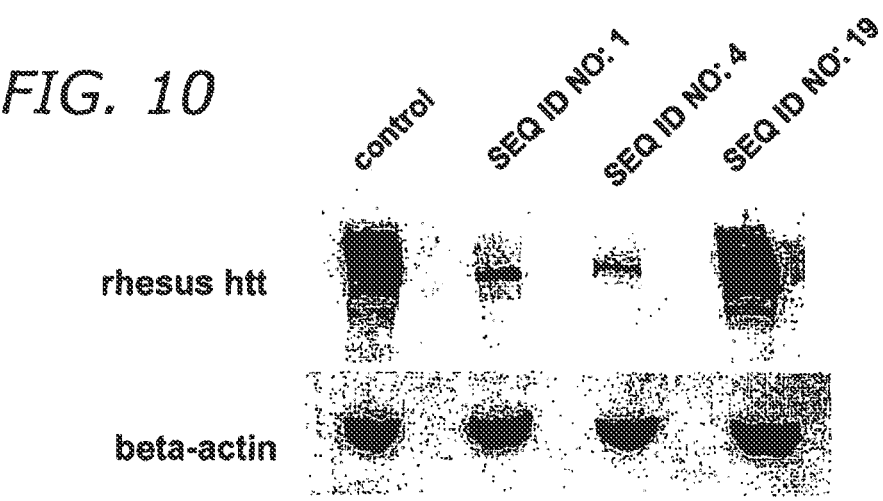
FIGS. 10 and 11 show suppression of endogenous rhesus huntingtin protein expression in LLC-MK2 cells.
Figure 11:
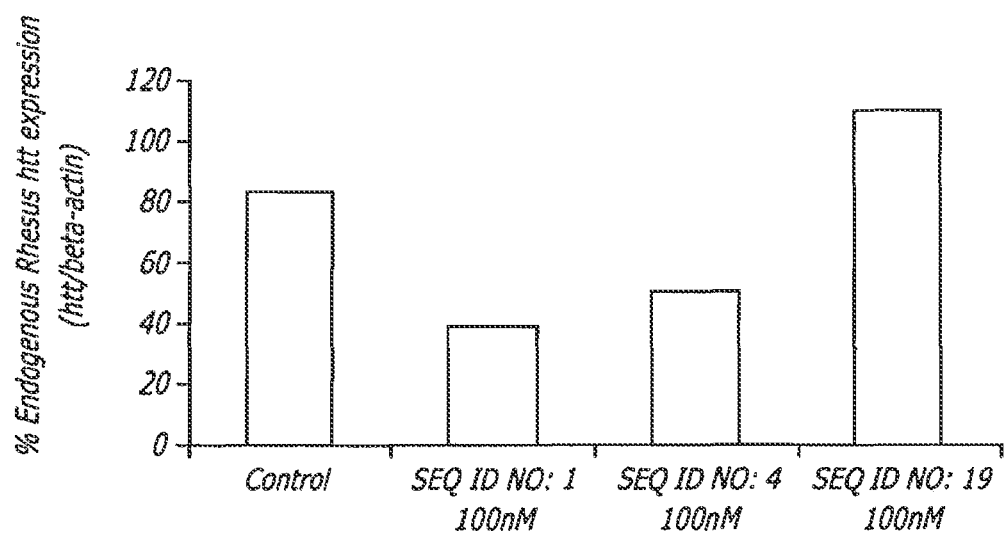

Next the ability of SEQ ID NO: 1 and SEQ ID NO: 4 to suppress endogenous protein expression was examined in LLC-MK2 cells again using western blot analysis. LLC-MK2 cells were transfected with 100 nM of either SEQ ID NO: 1, SEQ ID NO: 4 or SEQ ID NO: 19. An additional control consisted of extracts from untransfected cells. Protein was harvested and analyzed 48 hours post-transfection with 10 µg of total protein loaded per western blot well. Again, rhesus huntingtin protein expression was measured using the Chemicon® International (Temecula, Calif.) huntingtin antibody MAB2168 and β-actin was measured with Abcam® (Cambridge, Mass.) antibody 20272-100. As is evident on the western blot for rhesus huntingtin and β-actin shown in FIG. 10 both SEQ ID NO: 1 and SEQ ID NO: 4 suppress huntingtin protein expression. To quantify the amount of protein suppression, the level of rhesus huntingtin protein expression was normalized to β-actin expression. To do this the intensities of the bands on the autoradiogram of the western blot (FIG. 10) were measured by densitometry. As can be seen in FIG. 11, SEQ ID NO: 1 and SEQ ID NO: 4 both suppressed endogenous huntingtin protein expression when compared to cells transfected with control SEQ ID NO: 19 or to extract from untransfected cells.

Figure 12A:
FIG. 12 depicts a structure and construction of anti-HD (FIG. 12A) and control (FIG. 12B) shNA sequences.
Figure 12B:
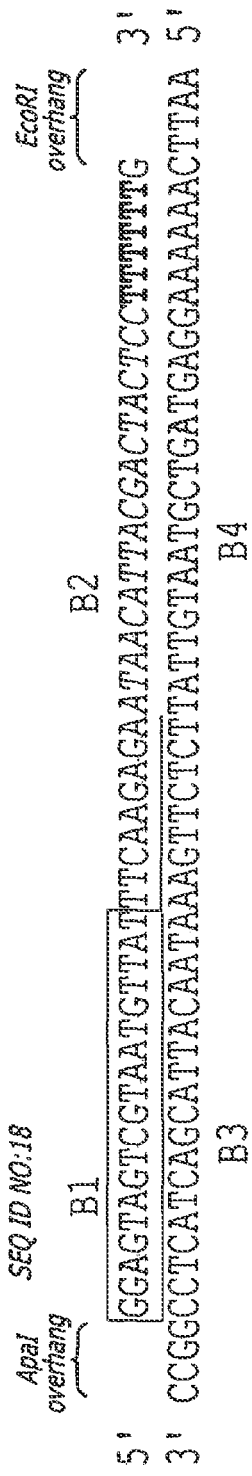
Figure 15:
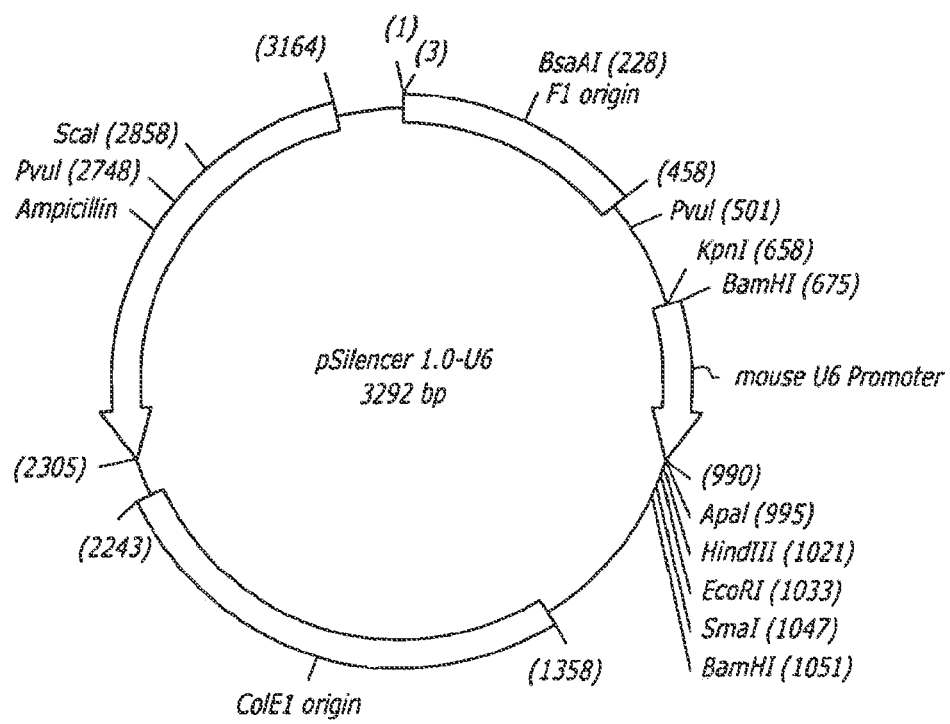
FIG. 15 shows a schematic description of a pSilencer 1.0-U6 plasmid that can be used in the preparation of anti-HD and control shNA sequences.

After effective nucleic acid sequences are identified as described above, effective sequences can be formatted into short hairpin nucleic acid ("shNA") structures. FIG. 12 shows SEQ ID NO: 4 reformatted and constructed as an anti-huntingtin shNA sequence (SEQ ID NO: 17; FIG. 12A). FIG. 12 also shows a control shNA sequence (SEQ ID NO: 18; FIG. 12B). The shNA sequences contain the siNA nucleic acid sequence (boxed sequence shown in black; in FIG. 12A, an originally effective nucleic acid sequence), a nine nucleotide loop (underlined), the reverse complement of the boxed nucleic acid sequence (italicized), and a Pol III terminator sequence (TTTTTT (bolded)). Four partially overlapping synthesized oligonucleotides (-A1, -A3, -A2, and -A4 in FIG. 12A and -B1, -B3, B2 and -B4 in FIG. 12B) can be used to assemble the shNAs. In two separate reactions, the 1/3 and 2/4 oligonucleotides for each shNA can be annealed. Referring to FIGS. 12A and 12B, the A1 and B1 oligonucleotides include the boxed sequences. The A2 and B2 oligonucleotides include the underlined nine nucleotide loop, the reverse complement of oligonucleotides A1 and B1 respectively, the bolded Pol III terminator sequence (TTTTTT) and the first G of the EcoRI site depicted in these FIGS. The A3 and B3 oligonucleotides of FIGS. 12A and 12B respectively include the ApaI overhang region, the reverse complement of the boxed A1/B1 sequences, and the reverse complement of the underlined nine nucleotide loop sequence. The A4 and 94 oligonucleotides include the reverse complement of the italicized portion of A2 and B2 respectively and the reverse complement (AAAAAA) of the bolded Pol III terminator sequence. Finally, the A4 and B4 oligonucleotides contain the EcoRI overhang region. ApaI and EcoRI restriction enzyme-compatible ends are included in the shNA structures for directional subcloning into a murine U6 promoter-containing shuttle vector (pSilencer1.0-U6; Ambion, Inc., Austin, Tex.; FIG. 15). The full-length shNAs (SEQ ID NOS: 17 and 18) then can be cloned into a ApaI/EcoRI-digested pSilencer vector using a three-way ligation reaction. The U6 promoter (murine or human) is used for constitutive high level expression of the nucleic acid sequences. In keeping with the present invention, a human H1 promoter can also be used. One non-limiting example of a shuttle vector containing the human U6 promoter is psiSTRIKE™ hmGFP from Promega Corporation (Madison, Wis.). One non-limiting example of a shuttle vector containing the human H1 promoter is pSilencer 3.0-H1 from Amibion, Inc, (Austin, Tex.).

While this example provides one embodiment of the nucleic acid sequences of the present invention in shNA format and a method for creating them, other configurations and methods also fall within the scope of the present invention. For example, in one embodiment, the loop structure of the shNA hairpin is 4 to 10 nucleotides in length. In another embodiment, the arms of the hairpin structures are less than approximately 30 nucleotides in length. In another embodiment, the arms of the hairpin structure are between 19 and 27 nucleotides in length. Thus, while a specific example is given, this example should not be interpreted to limit the scope of the present invention.

Figure 14:
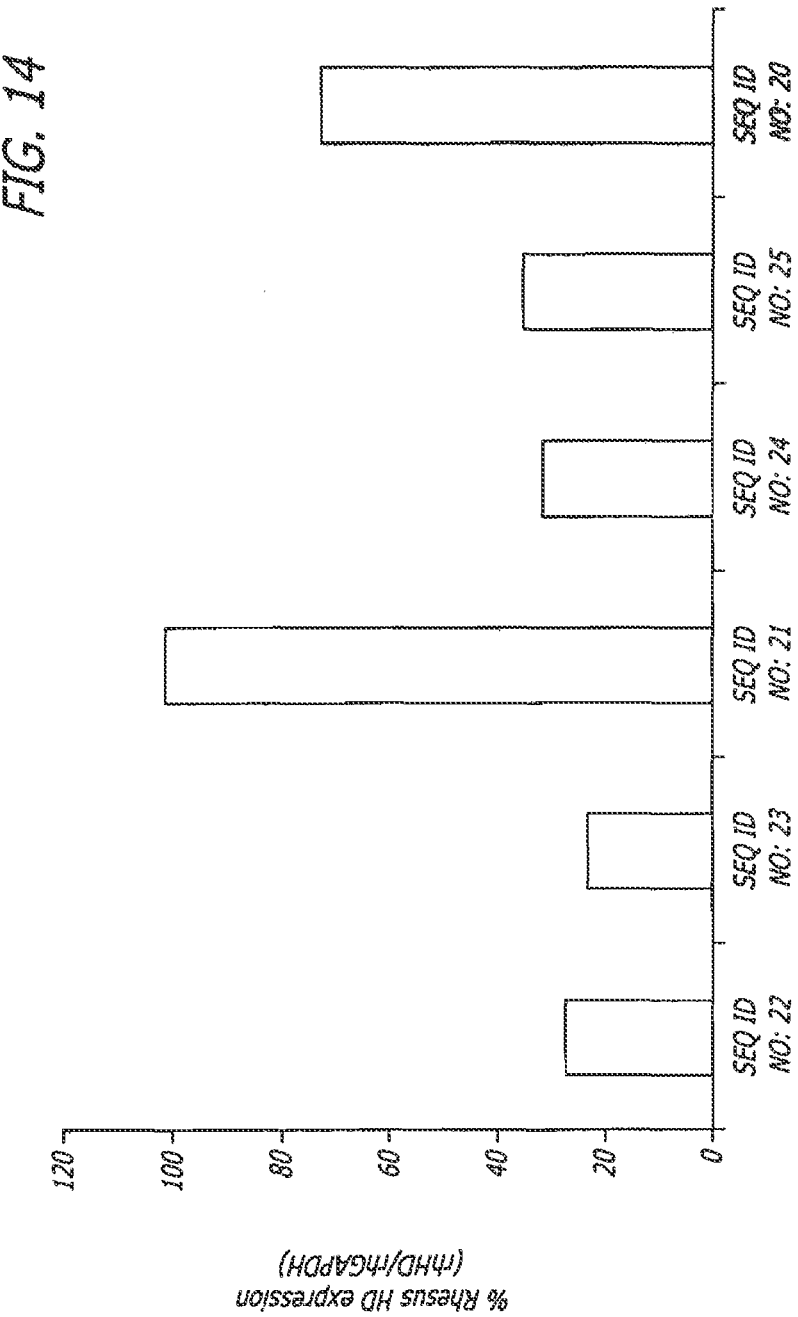
FIG. 14 shows suppression of the endogenous rhesus HD gene in LLC-MK2 cells transfected with a plasmid expressing 19 or 27 nucleotide length shNAs with EB4 or mir23 loop structures.

In the next described experiment, the ability of plasmids expressing shNA to suppress rhesus HD gene expression was examined. LLC-MK2 cells were transfected with a psiS-TRIKE™ hmGFP plasmid (Promega Corporation, Madison, Wis.) with one of two stem lengths (SEQ ID NO: 4 (19 nucleotides) or SEQ ID NO: 112 (27 nucleotides)) and one of two different loop structures (EB-4 or mir23). A scrambled control was also generated for each of the loop structures. Specifically, these scrambled control sequences included a 27 nucleotide sequence control (SEQ ID NO: 20) for EB4 (FIG. 13A) and a 19 nucleotide sequence control (SEQ ID NO: 21) for mir23 (FIG. 13B; SEQ ID NO: 21 is a modified version of control SEQ ID NO: 18). Thus, the whole of the transfected sequences in this study included SEQ ID NO, 20; SEQ ID NO. 21; SEQ ID NO. 22 (FIG. 13C; modified SEQ ID NO: 17-EB4 (as will be recognized by one of ordinary skill in the art, SEQ ID NO: 22 includes SEQ ID NO: 17 with modified overhang regions for subcloning into a different vector)); SEQ ID NO: 23 (FIG. 13D; modified SEQ ID NC): 17-mir23); SEQ ID NO: 24 (FIG. 13E; shNA-modified SEQ ID NO: 12-EB4); and SEQ ID NO: 25 (FIG. 13F; shNA-modified SEQ ID NO: 12-mir23). As can be seen in FIG. 14, all test plasmids suppressed rhesus HD gene expression when compared to control plasmids.

Figure 16:
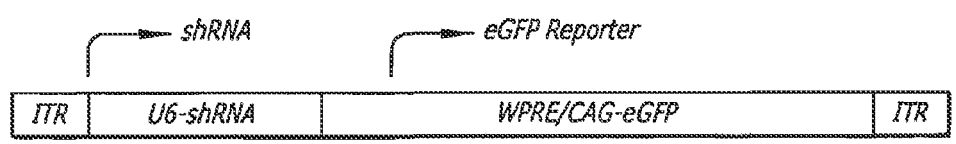
FIG. 16 shows an exemplary format of AAV viral constructs.

Next, a method to prepare viral production plasmids is described. This method is based on the method for producing the nucleic acid sequences in shNA formats described above. As will be understood by one of skill in the art, however, various known modifications of the described technique also fall within the scope of the present invention. First, the BamHI fragment (FIG. 15) containing the shNA expression cassette (murine U6 promoter, shNA sequence, and Pol III terminator sequence) from each of the pSilencer shuttle vectors (huntingtin and control) is recovered, blunted with T4 DNA polymerase, and subcloned into an AAV1/2 expression vector (deprAVE™; GeneDetect.com Ltd, Bradenton, Fla.). As shown in FIG. 16, in this example, in the final viral expression vector (used for virus production), the U6 promoter (murine or human) can drive the expression of the shNA and the Woodchuck enhancer/chicken .beta.-actin promoter can drive the expression of the enhanced green fluorescent protein (WPRE/CAG-eGFP). These expression cassettes can be flanked by viral inverted terminal repeats (ITR). The Woodchuck post-transcriptional regulatory element (WPRE) and the presence of a bovine growth hormone (BGH) polyadenlyation sequence ensure high transcription following cellular transduction. In alternative methods of the present invention, the expression cassette additionally contains a polyadenylation signal, such as a synthetic minimal polyadenylation signal. In another alternative embodiment of the present invention, the H1 promoter can be used.

Figure 17:
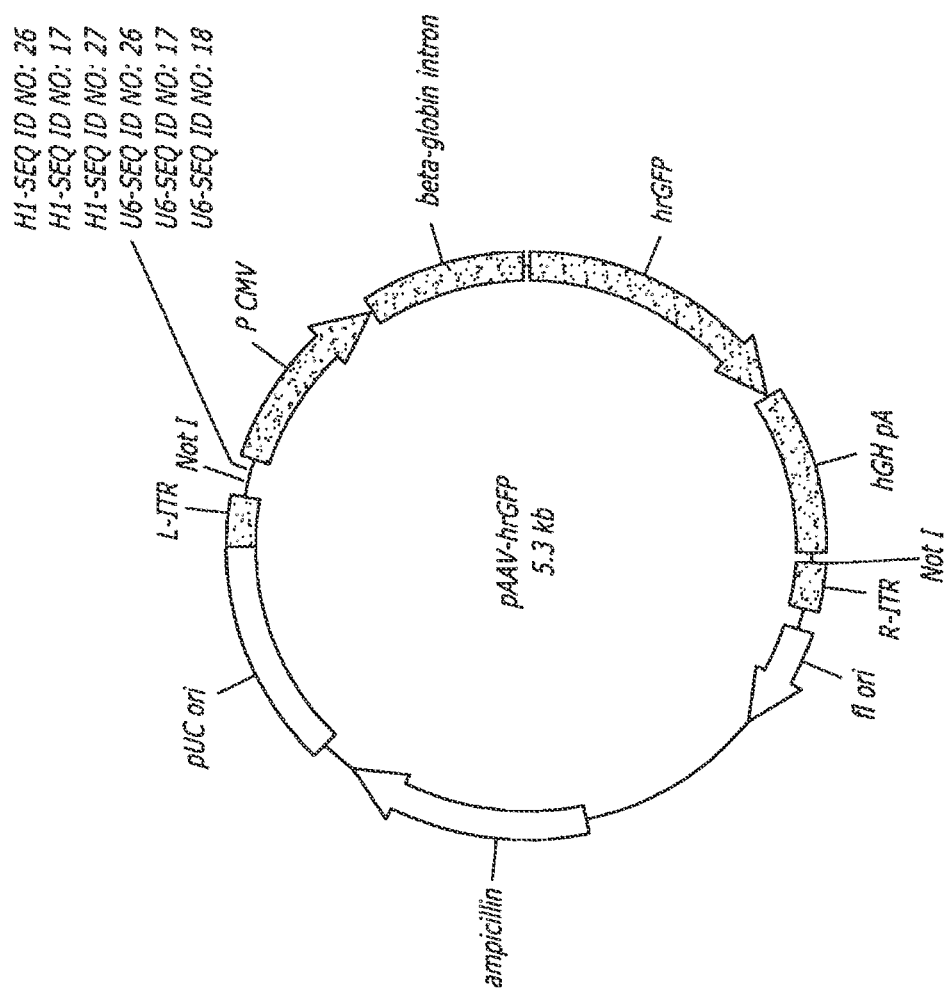
FIG. 17 shows a plasmid used to construct pAAV vectors and to generate AAV in accordance with the present invention.

FIG. 17 depicts a different plasmid, the plasmid used to construct pAAV vectors used in the Wowing experiments to generate AAV (pAAV-hrGFP, Stratagene, La Jolla, Calif.). Six different plasmids were constructed; 3 with an H1 promoter and 3 with a U6 promoter (human H1 promoter from Ambion (Austin, Tex.) and human U6 promoter from Promega (Madison, Wis.)). Specifically, the following were subcloned into the depicted vector (1) U6-SEQ ID NO: 17; (2) U6-SEQ ID NO: 26 (SEQ ID NO: 26 is SEQ ID NO: 1 in an shRNA format; see FIG. 18A); (3) H1-SEQ ID NO: 17; (4) H1-SEQ ID NO: 26; (5) U6-SEQ ID NO: 18 (scrambled shNA control); and (6) H1-SEQ ID NO: 27 (SEQ ID NO: 27 is a scrambled SEQ ID NO: 1 shNA control; see FIG. 18B). In this instance this was done by removing a cassette containing the promoter and the shNA sequence from the appropriate psiSTRIKE™ or pSilencer 3.0 shNA expressing vector with PvuII. This PvuII fragment was then subcloned into the blunted MluI site of pAAV-hrGFP (Stratagene, La Jolla, Calif.). Directionality was confirmed by restriction digest mapping and sequence analysis.

Figure 19:
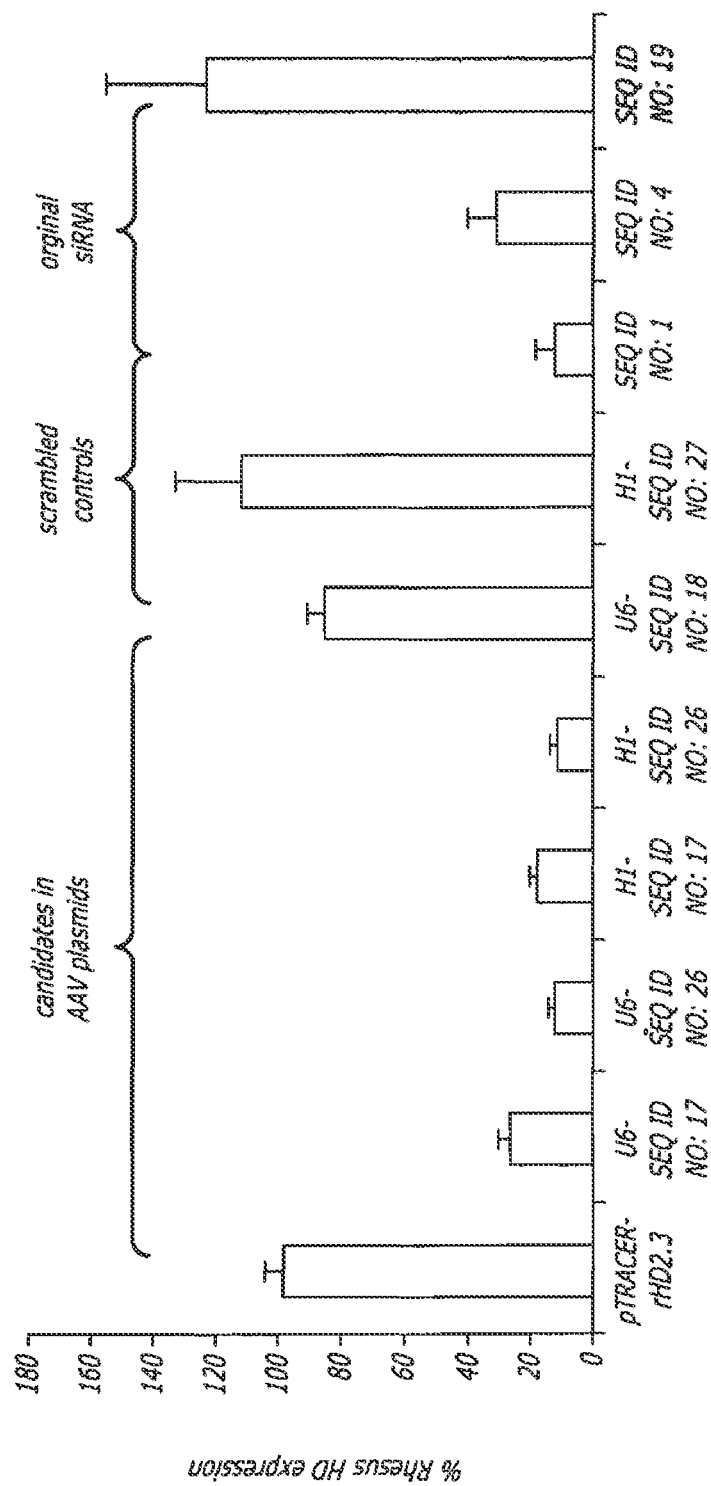
FIG. 19 shows suppression of exogenous rhesus HD by pAAV plasmids.

These six pAAV plasmids were co-transfected into HEK293T cells along with pTRACER-rhHD (FIG. 1). As controls, two siRNAs (SEQ ID NOS: 1 or 4) and the non-sense scrambled control (SEQ ID NO: 19) were also transfected into HEK293T pTRACER-rhHD was also transfected alone as a control. RNA was collected 48 hours post transfection and the suppression of rhesus HD gene expression (on the pTRACER plasmid) was measured by realtime PCR and normalized to the amount of GFP expressed from the pTRACER-rhHD plasmid. As can be seen in FIG. 19, pAAV plasmids containing U6-SEQ ID NO: 17; U6-SEQ ID NO: 26; H1-SEQ ID NO: 17; and H1-SEQ ID NO: 26 were as effective at suppressing exogenous rhesus HD gene expression as previously tested SEQ ID NO: 1 and SEQ ID NO: 4. pAAV plasmids expressing scrambled control sequences did not suppress exogenous rhesus HD gene expression.

Figure 20:
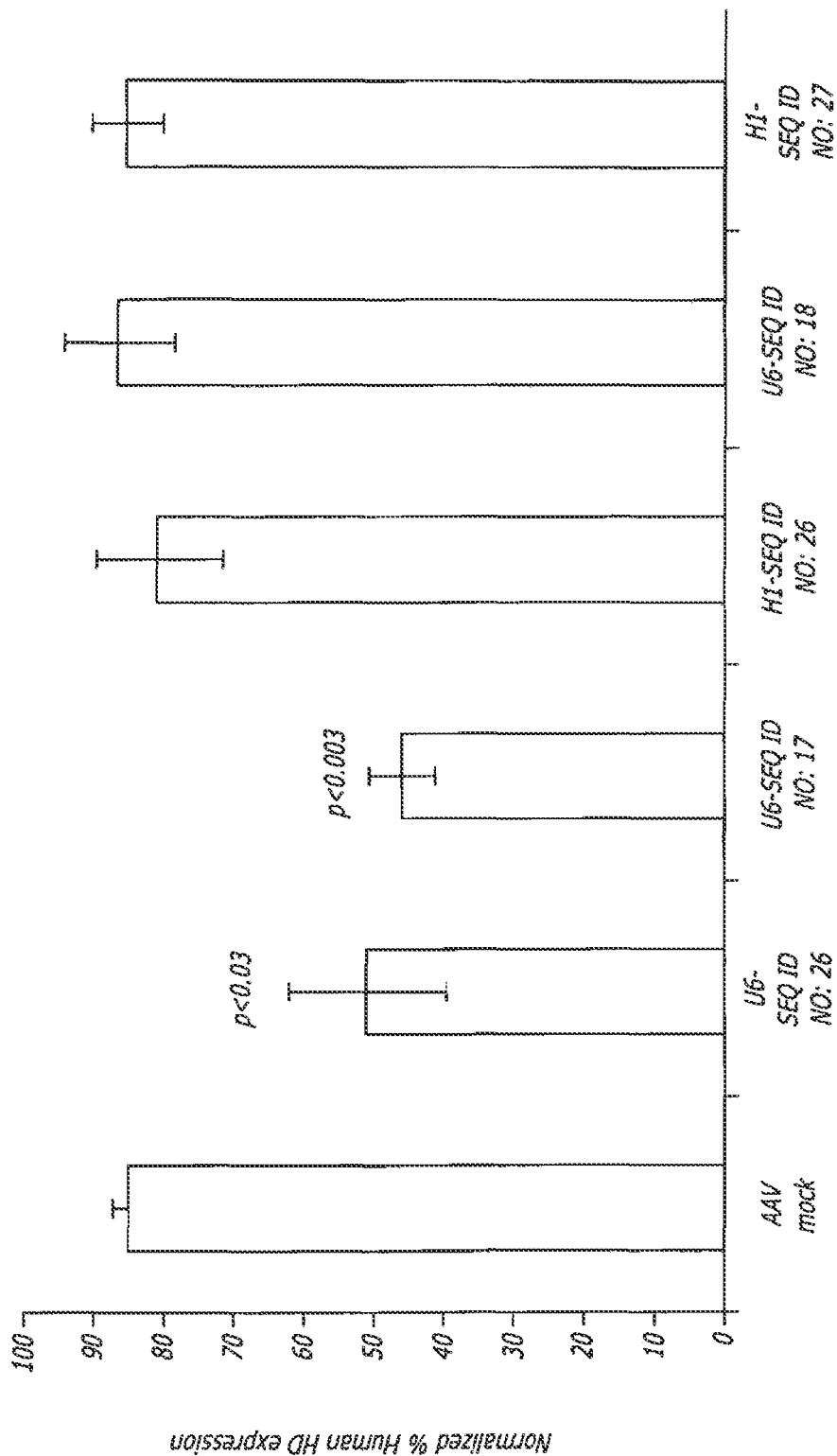
FIG. 20 shows suppression of endogenous human HD in HeLa cells and HEK293T cells by recombinant adeno-associated virus (AAV) expressing anti-HD shNA.

Next, the described pAAV plasmids along with the required pHELPER and REPCAP plasmids were used to generate recombinant adeno-associated virus (AAV) with serotype 1. Five separate AAV viruses were generated. These viruses were engineered to express U6-SEQ ID NO: 26; U6-SEQ ID NO: 17; H1-SEQ ID NO: 26; U6-SEQ ID NO: 18 (shNA control) or H1-SEQ ID NO: 27 (shNA control). The ability of these viruses to suppress endogenous human HD gene expression in HeLa cells and HEK293T cells was examined. 5e5 cells in a well of a 6-well plate were transduced with ~5e9 virions by directly adding the virus to the well of cells in 1 ml of Dulbecco's Modified Eagle Medium (DMEM) cell culture media supplemented with 2% fetal bovine serum (FBS). This plate was incubated at 37° C., 5% $CO_2$ for 2 hours with gentle mixing by rocking every 30 minutes. Following this 2 hour incubation, 1 ml of DMEM cell culture media supplemented with 18% FBS was added to each well yielding a final FBS concentration of 10%. Growth of the transduced cells was continued at 37° C., 5% $CO_2$. RNA was collected 72 hours post transduction and used to make cDNA by standard methods. The cDNAs were analyzed for HD and GAPDH expression levels by realtime PCR methods. Endogenous HD expression was normalized to endogenous GAPDH expression. As shown in FIG. 20, U6-SEQ ID NO: 26 and U6-SEQ ID NO: 17 were effective at suppressing endogenous human gene expression. P values were determined by comparison to the mock transduced data set. In this experiment, even though H1-SEQ ID NO: 26 did not significantly suppress endogenous human HD expression in vitro, its potential effectiveness in vivo should not be discounted especially in light of literature indicating a potential disconnect between in vitro and in vivo activity. See, for example, Wooddell et al., 334 Biochem. and Biophys. Res. Comm. 117-27 (2005).

The siNA sequences and molecules of the present invention can be manipulated to enhance their uptake into the RISC complex. Specifically, manipulating the 3 prime terminal nucleotide of the sense strand can be highly advantageous. Preferential entry of the guide, or antisense, strand into RISC can be achieved by introducing 3 prime mismatches in the sense strand while maintaining perfect base pairing (of the antisense strand and the intended mRNA target) at the 5 prime terminus of the antisense strand. This maximizes entry of the antisense strand into the RISC complex, while also reducing potential off-target inhibition by the sense strand.

Physical methods to introduce nucleic acid molecules and/or their carriers (i.e., vectors) into eukaryotic cells are known in the art. Some of these methods include, without limitation, calcium phosphate or calcium chloride co-precipitation, DEAE-dextran-mediated transfection, cationic lipid-mediated transfection, lipofection, protoplast fusion, particle bombardment, microinjection, liposome fusion, biolistics and other suitable methods found in, for example, Sambrook, et al. (Molecular Cloning: A Laboratory Manual, 2nd, ed, Cold Spring Harbor Laboratory, Cold Spring Harbor Laboratory Press, Cold Spring Harbor, N.Y., 1989), and other laboratory manuals. Further, biological methods to introduce nucleic acid molecules into a cell include the use of viral vectors. For mammalian gene therapy, viral vectors, and especially retroviral vectors, have become the most widely used method for inserting genes into mammalian, e.g., rhesus monkey or human cells. Other viral vectors can be derived from poxviruses, herpes simplex virus I, adenoviruses and adeno-associated viruses, and the like (see, for example, Boenisch et al., U.S. Pat. No. 5,350,674 and Wilson et al., U.S. Pat. No. 5,585,362 which are hereby incorporated by reference). Embodiments of the present invention also can be delivered through the use of liposomes, polyethyleneimine, by iontophoresis, or by incorporation into other vehicles, such as hydrogels, cyclodextrins, biodegradable nanocapsules, and bioadhesive microspheres. Nucleic acid molecules also can be directly delivered to cells or tissues with or without the aforementioned vehicles. The nucleic acid molecules/vehicle combinations can be locally delivered by catheter and drug pump systems, delivered by direct local injection or through the use of polymers and/or drug-eluting stents.

The nucleic acid sequences, molecules, expression cassettes and vectors of the present invention can be used to suppress HD gene expression and resulting huntingtin formation. The nucleic acid sequences, molecules, expression cassettes and vectors of the present invention also can be used in the study of HD pathogenesis. Further, the nucleic acid sequences, molecules, expression cassettes and vectors of the present invention also may be administered to prevent or treat the symptoms of HD. When used as a potential treatment, the amount of these agents administered as well as the timing of their delivery will vary depending on various factors including, for example and without limitation, the composition chosen, the weight, physical condition, and age of the patient, and whether prevention or treatment is desired as well as other factors known to skilled practitioners. Administration of the therapeutic agents can be continuous or intermittent. The administration of the agents of the invention can be essentially continuous over a preselected period of time or can be in a series of spaced doses. Further, both local and systemic administration can be appropriate for use within the present invention. Such factors can be determined by the researcher or treating physician.

A pre-clinical study of the safety of suppressing huntingtin protein expression in the normal adult rhesus monkey brain was conducted. In this study, a 6 year old female rhesus monkey weighing approximately 3.9 kg was anesthetized and bilaterally infused with an anti-HD shRNA/GFP-containing recombinant adeno-associated virus (AAV) (AAV-U6-SEQ ID NO: 17 (serotype AAV1; $2.07 \times 10^{12}$ vg/ml; lot #J0531)) by stereotactic injection. Stereotactic targets were determined by presurgical MRI and included putamen (AP=17; L-11; DV1=20 and DV2=17) and caudate nucleus (AP=20.5; L=5.6; DV=17) sites. Injections (Hamilton syringe (100 µl) with 27 Ga needle (compression fitting)) were performed at 2 putamen sites (50 µl/site) using a single needle tract and 1 caudate site (50 µl) at a rate of 1 µl/min. Following this injection, the needle was left in place for at least 20 minutes and then withdrawn at a rate of 1 mm/min.

Twenty-eight days later, the animal was deeply anesthetized with pentobarbital (1.5 ml intramuscular; 2 ml, intravenous) and transcardially perfused with heparinized ice-cold saline (4-6 L). Following perfusion and removal, the brain was placed into a container of ice-cold saline.

The right hemisphere of the brain was sectioned into 14-4 mm thick coronal sections and numbered 1-14 (rostral to caudal). A 14 G biopsy needle was then used to collected tissue punches from various brain regions. A total of 103 tissue punches was collected from the right hemisphere. Each tissue punch contained about 6 mg of tissue and was snap frozen in liquid nitrogen and stored at −80° C. until RNA was isolated.

Caudate; 20 punches (3 slabs)
Accumbens; 8 punches (2 slabs)
Cerebellum; 6 punches (1 slab)
Thalamus; 6 punches (1 slab)
Putamen; 20 punches (3 slabs)
GP; 5 punches (1 slab)
Occipital cx; 9 punches (1 slab)
Hippocampus; 6 punches (1 slab)
Nigra, 5 punches (1 slab)
Front. cx; 9 punches (1 s)
Motor cx; 9 punches (1 s)
Total n=103 punches RNA was isolated from tissue punches using the RNeasy Lipid Kit from Qiagen (Valencia, Calif.). Total RNA was used to generate cDNA using the Stratascript® First Strand cDNA synthesis kit from Stratagene (La Jolla, Calif.). The cDNAs were used to analyze expression levels of rhesus HD and GAPDH by realtime PCR. In addition, AAV expression was monitored by measuring the level of GFP expression. Rhesus HD expression was normalized to rhesus GAPDH expression and compared to a region not expressing the virus (GFP−).

The left hemisphere of the brain was sectioned into 4 blocks (rostral to caudal). Block 1 was 10 mm; blocks 2 and 3 were 16 mm; and block 4 was 20 mm. Each block was embedded in OCT, snap frozen in isopentane and stored at −80° C. Ten micron sections were then collected and placed onto laser microdissection (LMD) compatible slides. Tissue on the slides was fixed in ethanol (30 seconds in 75% ethanol; 30 seconds in 95% ethanol; and 30 seconds in 100% ethanol) with an air dry between steps. Slides were then screened to identify the ones containing brain regions of interest (i.e. caudate and putamen) and data on viral spread was obtained by following the expression of the marker gene (GFP). GFP positive regions were collected by LMD from the caudate and putamen.

RNA was isolated from GFP collected material using the PicoPure RNA isolation kit from Arcturus (Mountain View, Calif.). The RNA was quantified prior to the generation of cDNA. Typically about 10-80 ng of total RNA from the LMD collected material was isolated. cDNA was prepared using the Stratascript® QPCR cDNA synthesis kit from Stratagene (La Jolla, Calif.). HD expression was measured by realtime PCR and normalized to GAPDH expression in the same sample. To verify RNA collected from virally transduced cells were being analyzed, GFP realtime PCR to monitor GFP expression was also performed.

Figure 21:
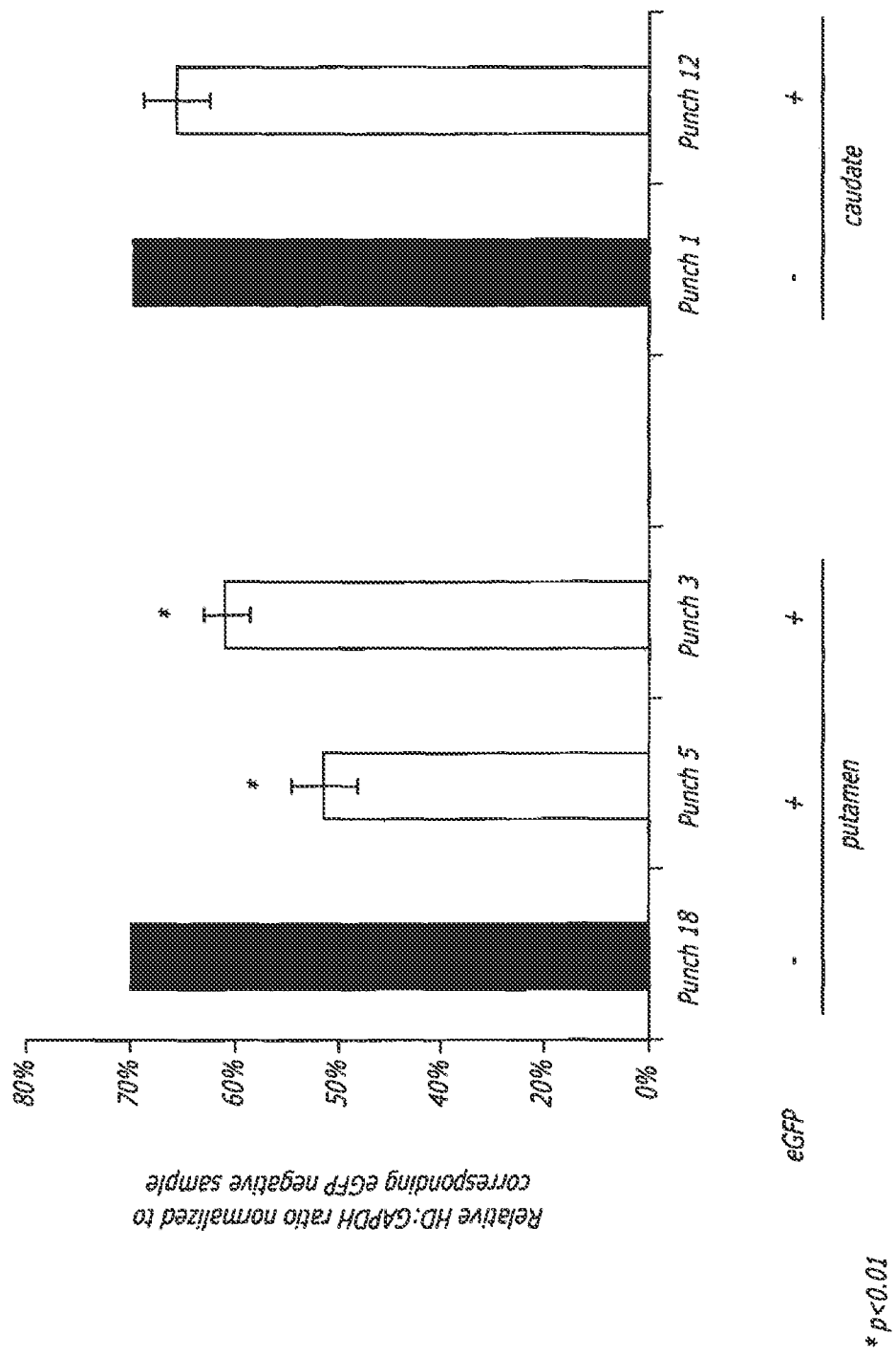
FIGS. 21 and 22 show in vivo suppression of rhesus HD gene expression by recombinant adeno-associated virus (AAV) expressing anti-HD shNA.
Figure 22:
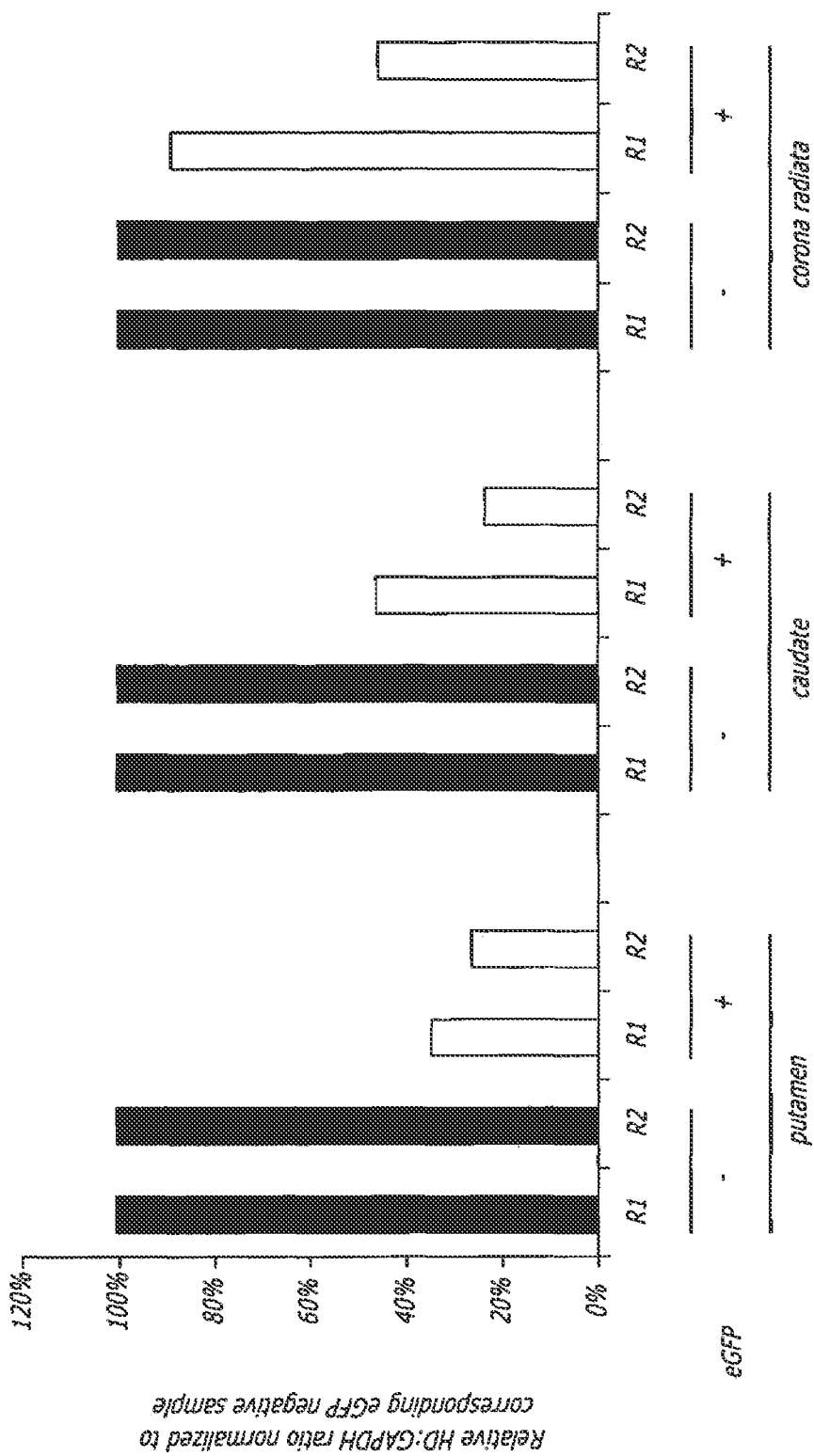

As can be seen in FIG. 21, when measured from samples obtained from tissue punches, in vivo HD gene expression was suppressed in the putamen but not the caudate. The likely reason suppression was not observed in the caudate is that the percent of cells expressing the virus within the collected punch is too low to elicit a detectable level of rhesus HD suppression. This was addressed by collecting GFP+ transduced cells by LMD. When measured from samples obtained through LMD, in vivo HD gene expression was suppressed in the putamen, caudate and corona radiate (FIG. 22; R1=replicate 1; R2=replicate 2). Together, these data demonstrate the feasibility and safety of in vivo HD gene expression in accordance with the methods and sequences of the present invention.

PROPHETIC EXAMPLE I

Pre-Clinical Test of the Safety of Suppressing Huntingtin Protein Expression in the Rhesus Monkey Brain Using shNA of the Invention A pre-clinical study of the safety of suppressing huntingtin protein expression in the normal adult rhesus monkey brain is conducted over a 12-month period. During the first three months of the study, six rhesus macaques (*Macaca mulatto*) are trained to perform the tasks of a commercially available computerized behavioral test battery (Monkey CANTAB, Model 80650, Lafayette Instruments, Lafayette, Ind.) that is based upon human neuropsychological tests (CANTAB, CeNeS, Cambridge, UK). The performance of these six monkeys on the test battery is compared to previously published performance norms for rhesus monkeys to verify that the monkey's cognitive abilities are within normal limits. See, for example, Weed et al., Brain Research: Cognitive Brain Research, 1999, Oct. 25; 8(3) 185-201.

Next, the monkeys are randomly assigned to one of two experimental groups: the first group of three monkeys receives intracranial injections of an adeno-associated virus (AAV) vector comprising an expression cassette containing an RNA polymerase III promoter driving expression of a short hairpin RNA transcript encoding for the shNA of SEQ ID NO: 17. A second expression cassette in the same vector encodes for a green fluorescent protein reporter gene. The second group of three monkeys receives intracranial injections of an adeno-associated virus vector comprising an expression cassette containing the same RNA polymerase III promoter driving expression of a control shNA sequence (SEQ ID NO:18). Also, a second expression cassette in this vector encodes for a green fluorescent protein reporter gene. The AAV vector is administered to the caudate nucleus and putamen of each hemisphere of each monkey's brain. The amount of AAV vector administered in each intracranial injection, and the surgical method and procedures for making these injections, are well-known to those skilled in the art.

After a one-week post-operative recovery time, the monkeys are repeatedly tested on a periodic basis using the Monkey CANTAB computerized testing battery for the remainder of the twelve-month study period. The cognitive and behavioral performance of each monkey over time is compared to its own pre-operative performance. No statistically significant decline in cognitive or behavioral performance measures is obtained for either the monkeys treated with the control shNA vector, or the monkeys treated with the anti-rhesus-HD shNA vector. This indicates that there are no significant cognitive or behavioral consequences of suppressing the expression of huntingtin protein in the caudate and putamen of the adult primate brain. Periodic neurological examinations of each monkey by skilled and qualified veterinarians unaware of the experimental group membership of each monkey also shows no neurological deficits in the monkeys.

At the end of the twelve-month study period, the monkeys are humanely terminated, and the brain of each monkey is removed and examined for abnormalities by trained pathologists. In addition, it is studied by fluorescence microscopy, immunohistochemistry, and molecular and biochemical assays. The regions of the brain in which the AAV vector effectively delivered the shNA are identified by fluorescence microscopy. This reveals expression of the green fluorescent protein reporter gene in substantial regions of the caudate nucleus and putamen in each hemisphere of each monkey's brain. Immunohistochemical staining for huntingtin protein, using antibodies and methods well-known to those skilled in the art, shows reduced levels of huntingtin protein in the caudate and putamen of the monkeys who received the anti-rhesus-HD shNA vector, compared to the monkeys who received the control shNA vector, indicating suppression of huntingtin protein expression by the shNA of the invention. Finally, homogenized brain tissue samples from the caudate and putamen of each monkey's brain are assayed for levels of rhesus HD mRNA measured by quantitative reverse transcriptase polymerase chain reaction (qRT-PCR) assay, and for levels of rhesus huntingtin protein measured by Western blotting, using methods well-known to those skilled in the art. These assays show the expression of HD mRNA and huntingtin protein is significantly reduced in the caudate and putamen of the monkeys who received the anti-rhesus-HD shNA vector, compared to the monkeys who received the control shNA vector. These data further confirm that the shNA vector of the invention suppresses the expression of huntingtin protein in the caudate and putamen of the monkeys receiving the antirhesus-HD shNA vector. Because this suppression of huntingtin protein in the caudate and putamen of the rhesus monkeys does not result in corresponding cognitive or behavioral deficits, or other observable neurological abnormalities or brain tissue pathology, the safety of suppressing huntingtin protein in these regions of the adult primate brain is established.

PROPHETIC EXAMPLE 2

Treatment of Huntington's Disease ("HD") in Human Patients Using shNA of the Invention Once the safety of suppressing huntingtin protein in the caudate and putamen of the adult primate brain is established in rhesus monkeys, the same shNA expression cassette that is used in the pre-clinical safety tests in rhesus monkeys is engineered into an AAV vector using methods well-known to those skilled in the art. This AAV vector comprises an expression cassette containing an RNA polymerase III promoter driving expression of a short hairpin RNA transcript encoding for the shNA of SEQ ID NO: 17. The AAV vector optionally does not contain a second expression cassette encoding for a green fluorescent protein reporter gene, because this expression cassette is not needed for the treatment of HD in patients.

It is to be especially understood that because the shNA sequence encoded by SEQ ID NO: 17 contains the siNA target region of SEQ ID NO: 4, and the sequence of SEQ ID NO: 4 is 100% homologous with corresponding sequences within both the *Macaca mulatto* and the *Homo sapiens* HD gene, an AAV vector comprising an expression cassette containing SEQ ID NO: 17 is effective at suppressing the expression of the *Homo sapiens* HD gene and huntingtin protein, as well as the *Macaca mulatto* HD gene and huntingtin protein.

Following safety and dose-escalation trials in human patients in which the safety of administering the AAV vector comprising SEQ ID NO: 17 is established, clinical trials evaluating the clinical efficacy of the invention in treating HD in human patients are conducted. In these trials, the AAV vector can be administered to the human patient's brain according to the systems and methods disclosed in U.S. Patent Publication Nos. 20040162255 and 20040220132. These trials establish that suppression of huntingtin protein in the caudate and putamen of human patients afflicted with HD using the nucleic acid molecules, expression cassettes, or vectors of the present invention is effective at arresting and partially reversing the cognitive and motor deficits in patients treated after onset of these symptoms of the disease. These results are consistent with findings obtained in conditional transgenic mouse models of HD, in which expression of a mutant HD transgene results in a disease phenotype, after which suppressing the expression of the mutant HD transgene results in reversal of the disease phenotype and improvement of the mice. Yamamoto et al., Cell, 2000, Mar. 31; 101(1):57-66.

It is to be understood that the present invention is not limited to the particular embodiments, materials, and examples described herein, as these can vary. For example, the nucleic acid molecules of the present invention can be created in a variety of formats and lengths. Indeed, those skilled in the art will recognize that the most important attribute of the nucleic acid molecules of the present invention is their ability to enter the RISC complex and also complementarily bind to the mRNA sequences of interest to induce an RNA interference effect, resulting in reduction of the mRNA stability and/or the translation rate of these sequences. The phrase "complementarily bind" as used herein, refers to the abilities of the nucleic acid molecules to form hydrogen bond(s) with mRNA sequences by either traditional Watson-Crick pairing or other non-traditional types.

It also is to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a sequence" or "an shNA" is a reference to one or more sequences or shNAs and includes equivalents thereof known to those skilled in the art and so forth.

Unless defined otherwise, all technical terms used herein have the same meanings as commonly understood by one of ordinary skill in the art to which this invention belongs. Specific methods, devices, and materials are described, although any methods and materials similar or equivalent to those described herein can be used in the practice or testing of the present invention.

We claim:

1. An isolated nucleic acid duplex comprising a first strand of nucleic acid and a second strand of nucleic acid, wherein the first strand comprises at least 19 contiguous nucleotides encoded by SEQ ID NO: 8, and the second strand is complementary to at least 15 contiguous nucleotides within said at least 19 contiguous nucleotides of SEQ ID NO: 8 of the first strand.

2. The isolated nucleic acid duplex of claim 1, wherein the first strand is connected to the second strand by means of a loop.

3. The isolated nucleic acid duplex of claim 1, wherein the second strand is complementary to 19 nucleotides within SEQ ID NO: 8 of the first strand.

4. A vector encoding the isolated nucleic acid duplex of claim 1.

5. The vector of claim 4, wherein the vector is a viral vector.

6. The vector of claim 5, wherein the viral vector is an adeno-associated viral vector.

7. A method for suppression of huntingtin in a cell comprising administering to the cell an isolated nucleic acid duplex of claim 1.

8. The method according to claim 7, wherein the cell is within a mammalian patient.

9. The method according to claim 8, wherein said mammalian patient is a human patient.

10. The method according to claim 7, wherein the nucleic acid duplex of claim 1 is within a vector.

11. The method of claim 10, wherein said vector is complexed with cationic lipids or packaged within liposomes microparticles, or microcapsules.

12. The isolated nucleic acid duplex of claim 1, wherein the nucleic acid duplex is between 19 and 30 base pairs in length.

13. The isolated nucleic acid duplex of claim 12, wherein the first strand is connected to the second strand by means of a loop.

14. The isolated nucleic acid duplex of claim 12, wherein the second strand is complementary to 19 nucleotides within SEQ ID NO: 8 of the first strand.

15. A vector encoding the isolated nucleic acid duplex of claim 12.

16. The vector of claim 15, wherein the vector is a viral vector.

17. The vector of claim 16, wherein the viral vector is an adeno-associated viral vector.

18. A method for suppression of huntingtin in a cell comprising administering to the cell an isolated nucleic acid duplex of claim 12.

19. The method according to claim 18, wherein the cell is within a mammalian patient.

20. The method according to claim 19, wherein said mammalian patient is a human patient.

21. The method according to claim 18, wherein the nucleic acid duplex of claim 1 is within a vector.

22. The method of claim 21, wherein said vector is complexed with cationic lipids or packaged within liposomes microparticles, or microcapsules.

* * * * *

SEQUENCE LISTING

```
<160> NUMBER OF SEQ ID NOS: 27

<210> SEQ ID NO 1
<211> LENGTH: 19
<212> TYPE: DNA
<213> ORGANISM: Homo sapiens

<400> SEQUENCE: 1
tgacagcagt gttgataaa                                                   19

<210> SEQ ID NO 2
<211> LENGTH: 19
<212> TYPE: DNA
<213> ORGANISM: Homo sapiens

<400> SEQUENCE: 2
aagaacgagt gctcaataa                                                   19
```

```
<210> SEQ ID NO 3
<211> LENGTH: 19
<212> TYPE: DNA
<213> ORGANISM: Homo sapiens

<400> SEQUENCE: 3
tttatgaact gacgttaca                                                  19

<210> SEQ ID NO 4
<211> LENGTH: 19
<212> TYPE: DNA
<213> ORGANISM: Homo sapiens

<400> SEQUENCE: 4
ggagtattgt ggaacttat                                                  19

<210> SEQ ID NO 5
<211> LENGTH: 19
<212> TYPE: DNA
<213> ORGANISM: Homo sapiens

<400> SEQUENCE: 5
gagtattgtg gaacttata                                                  19

<210> SEQ ID NO 6
<211> LENGTH: 19
<212> TYPE: DNA
<213> ORGANISM: Homo sapiens

<400> SEQUENCE: 6
agaccgtgtg aatcattgt                                                  19

<210> SEQ ID NO 7
<211> LENGTH: 19
<212> TYPE: DNA
<213> ORGANISM: Homo sapiens

<400> SEQUENCE: 7
ggttacagct cgagctcta                                                  19

<210> SEQ ID NO 8
<211> LENGTH: 19
<212> TYPE: DNA
<213> ORGANISM: Homo sapiens

<400> SEQUENCE: 8
ggttttgtta aaggccttc                                                  19

<210> SEQ ID NO 9
<211> LENGTH: 27
<212> TYPE: DNA
<213> ORGANISM: Homo sapiens

<400> SEQUENCE: 9
tgacagcagt gttgataaat ttgtgtt                                         27

<210> SEQ ID NO 10
<211> LENGTH: 27
<212> TYPE: DNA
<213> ORGANISM: Homo sapiens

<400> SEQUENCE: 10
aagaacgagt gctcaataat gttgtca                                         27
```

```
<210> SEQ ID NO 11
<211> LENGTH: 27
<212> TYPE: DNA
<213> ORGANISM: Homo sapiens

<400> SEQUENCE: 11
tttatgaact gacgttacat catacac                                            27

<210> SEQ ID NO 12
<211> LENGTH: 27
<212> TYPE: DNA
<213> ORGANISM: Homo sapiens

<400> SEQUENCE: 12
ggagtattgt ggaacttata gctggag                                            27

<210> SEQ ID NO 13
<211> LENGTH: 27
<212> TYPE: DNA
<213> ORGANISM: Homo sapiens

<400> SEQUENCE: 13
gagtattgtg gaacttatag ctggagg                                            27

<210> SEQ ID NO 14
<211> LENGTH: 27
<212> TYPE: DNA
<213> ORGANISM: Homo sapiens

<400> SEQUENCE: 14
agaccgtgtg aatcattgtc tgacaat                                            27

<210> SEQ ID NO 15
<211> LENGTH: 27
<212> TYPE: DNA
<213> ORGANISM: Homo sapiens

<400> SEQUENCE: 15
ggttttgtta aaggccttca tagcgaa                                            27

<210> SEQ ID NO 16
<211> LENGTH: 19
<212> TYPE: DNA
<213> ORGANISM: Homo sapiens

<400> SEQUENCE: 16
aatcctcctt cgtattata                                                     19

<210> SEQ ID NO 17
<211> LENGTH: 54
<212> TYPE: DNA
<213> ORGANISM: Homo sapiens

<400> SEQUENCE: 17
ggagtattgt ggaacttatt tcaagagaat aagttccaca atactccttt tttg              54

<210> SEQ ID NO 18
<211> LENGTH: 54
<212> TYPE: DNA
<213> ORGANISM: Homo sapiens

<400> SEQUENCE: 18
ggagtagtcg taatgttatt tcaagagaat aacattacga ctactccttt tttg              54
```

```
<210> SEQ ID NO 19
<211> LENGTH: 19
<212> TYPE: DNA
<213> ORGANISM: Artificial
<220> FEATURE:
<223> OTHER INFORMATION: Non-sense scrambled control sequence

<400> SEQUENCE: 19
tagcgactaa acacatcaa                                                   19

<210> SEQ ID NO 20
<211> LENGTH: 74
<212> TYPE: DNA
<213> ORGANISM: Homo sapiens

<400> SEQUENCE: 20
accgggagta gtcgtaatgt tatgcgaagt gttcaagaga cacttcgcat aacattacga     60
ctactccttt tttc                                                        74

<210> SEQ ID NO 21
<211> LENGTH: 59
<212> TYPE: DNA
<213> ORGANISM: Homo sapiens

<400> SEQUENCE: 21
accgggagta gtcgtaatgt tatcttcctg tcaataacat tacgactact ccttttttc      59

<210> SEQ ID NO 22
<211> LENGTH: 58
<212> TYPE: DNA
<213> ORGANISM: Homo sapiens

<400> SEQUENCE: 22
accgggagta ttgtggaact tatttcaaga gaataagttc cacaatactc cttttttc       58

<210> SEQ ID NO 23
<211> LENGTH: 59
<212> TYPE: DNA
<213> ORGANISM: Homo sapiens

<400> SEQUENCE: 23
accgggagta ttgtggaact tatcttcctg tcaataagtt ccacaatact ccttttttc      59

<210> SEQ ID NO 24
<211> LENGTH: 74
<212> TYPE: DNA
<213> ORGANISM: Homo sapiens

<400> SEQUENCE: 24
accgggagta ttgtggaact tatagctgga gttcaagaga ctccagctat aagttccaca    60
atactccttt tttc                                                       74

<210> SEQ ID NO 25
<211> LENGTH: 75
<212> TYPE: DNA
<213> ORGANISM: Homo sapiens

<400> SEQUENCE: 25
accgggagta ttgtggaact tatagctgga gcttcctgtc actccagcta taagttccac    60
aatactcctt ttttc                                                      75

<210> SEQ ID NO 26
```

```
<211> LENGTH: 58
<212> TYPE: DNA
<213> ORGANISM: Homo sapiens

<400> SEQUENCE: 26
accgtgacag cagtgttgat aaattcaaga gatttatcaa cactgctgtc atttttc        58

<210> SEQ ID NO 27
<211> LENGTH: 58
<212> TYPE: DNA
<213> ORGANISM: Homo sapiens

<400> SEQUENCE: 27
accgtgacga agtcgtgatt aaattcaaga gatttaatca cgacttcgtc atttttc        58
```